(12) United States Patent
Paspa et al.

(10) Patent No.: US 11,331,496 B2
(45) Date of Patent: May 17, 2022

(54) BIOSTIMULATOR FEEDTHROUGH HAVING INTEGRATED ELECTRODE CUP

(71) Applicant: Pacesetter, Inc., Sylmar, CA (US)

(72) Inventors: Paul Paspa, Los Gatos, CA (US);
Thomas B. Eby, Mountain View, CA (US); Matthew G. Fishler, Scotts Valley, CA (US); Carl Lance Boling, San Jose, CA (US); Thomas Robert Luhrs, Santa Rosa, CA (US); Russell Klehn, Valencia, CA (US); Tyler J. Strang, Valencia, CA (US); Arees Garabed, North Hills, CA (US); Kavous Sahabi, Winnetka, CA (US); Brett Villavicencio, Valencia, CA (US); Wes Alleman, Saugus, CA (US); Alex Soriano, Ventura, CA (US); Matthew R. Malone, Snohomish, WA (US); Conor P. Foley, Santa Clarita, CA (US)

(73) Assignee: Pacesetter, Inc., Sylmar, CA (US)

(*) Notice: Subject to any disclaimer, the term of this patent is extended or adjusted under 35 U.S.C. 154(b) by 116 days.

(21) Appl. No.: 16/662,282

(22) Filed: Oct. 24, 2019

(65) Prior Publication Data
US 2020/0129763 A1    Apr. 30, 2020

Related U.S. Application Data

(60) Provisional application No. 62/895,409, filed on Sep. 3, 2019, provisional application No. 62/750,681, filed on Oct. 25, 2018.

(51) Int. Cl.
*A61N 1/05* (2006.01)
*A61N 1/362* (2006.01)
(Continued)

(52) U.S. Cl.
CPC ......... *A61N 1/3629* (2017.08); *A61N 1/0568* (2013.01); *A61N 1/0573* (2013.01);
(Continued)

(58) Field of Classification Search
CPC .. A61N 1/0568; A61N 1/0573; A61N 1/0575; A61N 1/3629; A61N 1/37205;
(Continued)

(56) References Cited

U.S. PATENT DOCUMENTS

| 4,243,042 A | 1/1981 | Ware |
| 6,622,046 B2 | 9/2003 | Fraley et al. |

(Continued)

*Primary Examiner* — Carl H Layno
*Assistant Examiner* — Anh-Khoa N Dinh
(74) *Attorney, Agent, or Firm* — Vierra Magen Marcus LLP

(57) ABSTRACT

A biostimulator, such as a leadless cardiac pacemaker, including an electrical feedthrough assembly mounted on a housing, is described. An electronics compartment of the housing can contain an electronics assembly to generate a pacing impulse, and the electrical feedthrough assembly can include an electrode tip to deliver the pacing impulse to a target tissue. A monolithically formed electrode body can have a pin integrated with a cup. The pin can be electrically connected to the electronics assembly, and the cup can be electrically connected to the electrode tip. Accordingly, the biostimulator can transmit the pacing impulse through the monolithic pin and cup to the target tissue. The cup can hold a filler having a therapeutic agent for delivery to the target tissue and may include retention elements for maintaining the filler at a predetermined location within the cup.

24 Claims, 12 Drawing Sheets

(51) Int. Cl.
*A61N 1/372* (2006.01)
*A61N 1/375* (2006.01)

(52) U.S. Cl.
CPC ......... *A61N 1/0575* (2013.01); *A61N 1/3754* (2013.01); *A61N 1/37512* (2017.08); *A61N 1/37518* (2017.08)

(58) Field of Classification Search
CPC ............ A61N 1/37512; A61N 1/37518; A61N 1/3754; A61N 1/3756
See application file for complete search history.

(56) References Cited

U.S. PATENT DOCUMENTS

| | | | |
|---|---|---|---|
| 6,852,925 B2 | 2/2005 | Wolf et al. | |
| 8,509,921 B2 | 8/2013 | Doerr | |
| 8,519,280 B2 | 8/2013 | Teske | |
| 9,345,185 B2 | 5/2016 | Prasannakumar et al. | |
| 9,844,659 B2 | 12/2017 | Grubac et al. | |
| 2008/0161886 A1* | 7/2008 | Stevenson | A61N 1/3718 607/60 |
| 2011/0029027 A1* | 2/2011 | Wengreen | A61N 1/3754 607/2 |
| 2012/0130438 A1* | 5/2012 | Seeley | A61N 1/3752 607/2 |
| 2014/0107723 A1* | 4/2014 | Hou | A61N 1/3756 607/28 |
| 2014/0163580 A1* | 6/2014 | Tischendorf | A61N 1/0551 606/129 |
| 2014/0296955 A1* | 10/2014 | Jang | A61N 1/3756 607/120 |
| 2015/0116053 A1 | 4/2015 | Stevenson et al. | |
| 2015/0374976 A1* | 12/2015 | Regnier | A61N 1/3756 607/120 |
| 2017/0113032 A1 | 4/2017 | Sontheimer | |
| 2017/0294250 A1 | 10/2017 | Giese | |
| 2018/0280685 A1 | 10/2018 | Toy et al. | |

\* cited by examiner

BIOSTIMULATOR FEEDTHROUGH HAVING INTEGRATED ELECTRODE CUP

CROSS-REFERENCE TO RELATED APPLICATIONS

The present application claims priority to U.S. Provisional Patent Application No. 62/750,681, filed Oct. 25, 2018, and entitled "Bio stimulator Feedthrough Having Integrated Electrode Cup". The present application also claims priority to U.S. Provisional Patent Application No. 62/895,409, filed Sep. 3, 2019, and entitled "Biostimulator Feedthrough Having Integrated Electrode Cup". The contents of the above-mentioned patent applications are hereby incorporated by reference in their entirety.

FIELD

The present disclosure relates to biostimulators, an electrical feedthrough assembly and a method. More specifically, the present disclosure relates to leadless biostimulators having the electrical feedthroughs assembly (or short form: "electrical feedthrough"), and particularly a method for manufacturing the electrical feedthrough assembly.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

A pulse generator can have an electrical feedthrough to provide an electrical circuit path from an interior of a hermetically sealed battery container to an external lead connection. The electrical circuit path generally includes a conductor pin having an end within the sealed container and an end at the external connection.

Conventional pacemakers have several drawbacks, including a risk of lead or feedthrough pin breakage, complex connections between the leads and the feedthrough pins, and a risk of infection and morbidity due to the separate leads and pulse generator components. Many of the issues associated with conventional pacemakers are resolved by the development of a self-contained and self-sustainable biostimulator, or so-called leadless bio stimulators. The leadless bio stimulator can be attached to tissue within a dynamic environment, e.g., within a chamber of a beating heart. Electrical feedthroughs used to connect a pulse generator to a lead, however, may not include the features that are needed in a leadless biostimulator, where a pacing tip is effectively collocated with the feedthrough. For example, a conventional feedthrough may not include a container to deliver a therapeutic agent at the implant site.

SUMMARY

Embodiments concern an electrical feedthrough assembly with the features of the corresponding independent apparatus claims, a bio stimulator with the features of the corresponding further independent apparatus claims, and a method with the features of the independent method claim. Furthermore, embodiments concern another electrical feedthrough assembly with the features of the corresponding further independent apparatus claims, another bio stimulator with the features of the corresponding further independent apparatus claims, and another method with the features of the further independent method claim. Features and details of the present disclosure result from the sub claims, the description and the respective drawings. Features and details discussed with respect to the electrical feedthrough assembly(s) according to the disclosure therefore are also correlated with features and details as to the biostimulator(s), and the method(s) according to the disclosure, and vice versa.

According to the disclosure, an electrical feedthrough assembly for a biostimulator is provided.

The biostimulator can comprise an electrode body including a cup having an electrode wall extending distally from an electrode base around an electrode cavity located on a longitudinal axis, and a pin extending proximally from the electrode base along the longitudinal axis, wherein the cup and the pin are integrally formed such that the electrode body is monolithic.

According to another aspect of the disclosure, the electrical feedthrough assembly can further comprise an insulator having an insulator wall extending distally from an insulator base around the electrode wall, wherein the insulator base is proximal to the electrode base, wherein an insulator hole extends through the insulator base along the longitudinal axis, and wherein the pin extends through the insulator hole from the electrode base to a proximal end of the electrode body. Furthermore, a flange having a mounting wall can extend around the insulator wall.

Particularly, a gasket of the electrical feedthrough assembly can be provided having an annular body extending around the electrode wall, wherein the gasket is distal to the insulator wall and the mounting wall, and wherein the gasket includes a resilient material.

Advantageously, the electrical feedthrough assembly further comprises an electrode tip mounted on a distal end of the electrode body, wherein the electrode tip includes a tip hole extending through the electrode tip along the longitudinal axis from a distal tip end to a proximal tip end.

It is also possible that a first diameter of the tip hole at the distal tip end is less than a second diameter of the tip hole at the proximal tip end.

The electrical feedthrough assembly can further comprise one or more weeping holes extending through one or more of the electrode wall or the electrode tip along a transverse axis orthogonal to the longitudinal axis.

The electrical feedthrough assembly can further comprise a filler in the electrode cavity, wherein the filler includes a therapeutic agent in a silicone matrix.

The electrical feedthrough assembly can further comprise one or more retention features within the electrode cavity that maintain the filler at a predetermined location within the electrode cavity.

It can also be possible that the one or more retention features include one or more protrusions extending from the electrode wall and in contact with an outer surface of the filler.

It is also conceivable that the one or more protrusions include a plurality of protrusions spaced equidistantly about the longitudinal axis.

It can be intended that the one or more retention features include one or more tabs formed from the electrode wall and bent inwardly into the electrode cavity.

It is possible that the one or more retention features include a lip extending circumferentially about an interior surface of the electrode wall and into the electrode cavity.

It is possible that the one or more retention features include a coil disposed within the electrode cavity, wherein the coil extends along the longitudinal axis and is in contact with an outer surface of the filler.

It is also possible that the one or more retention features include a spring disposed within the electrode cavity, wherein the spring extends along the longitudinal axis and is in contact with an outer surface of the filler.

It is also possible that the one or more retention features include a first retention feature, which includes one or more dimples formed on the electrode wall, and a second retention feature that includes a coil inserted into an electrode cavity distal the filler.

It is also possible that the one or more retention features comprise three protrusions evenly distributed about the longitudinal axis.

It is also possible that the one or more retention features comprise three dimples evenly distributed about the longitudinal axis.

It is also possible that the one or more retention features comprise a first retention feature, which consists of three protrusions evenly distributed about the longitudinal axis, and a second retention feature comprising a coil inserted into the electrode cavity distal the filler.

It is also possible that the one or more retention features comprise a first retention feature, which comprises of three dimples evenly distributed about the longitudinal axis, and a second retention feature comprising a coil inserted into the electrode cavity distal the filler.

It is conceivable that the retention feature includes a spacer disposed within the electrode cavity, wherein the spacer includes a through hole extending along the longitudinal axis.

It is conceivable that the retention feature includes a tubular spacer disposed within the electrode cavity, wherein the tubular spacer includes a through hole extending along the longitudinal axis.

Furthermore, it can be provided that the retention feature is a first retention feature, the electrical feedthrough assembly further comprising a second retention feature within the electrode cavity that maintains the filler at the predetermined location within the electrode cavity.

It is also possible that the first retention feature is integrally formed with the electrode wall and the second retention feature is inserted into the electrode cavity.

It can be provided that the first retention feature is a plurality of protrusions extending inwardly toward the longitudinal axis and the second retention feature is a coil inserted into the electrode cavity distal the filler.

It may also be provided that the plurality of protrusions consists of three protrusions evenly distributed about the longitudinal axis.

According to a further aspect of the disclosure, a biostimulator is provided.

The biostimulator can comprise a housing having a longitudinal axis and containing an electronics compartment.

Furthermore, the biostimulator can comprise an electronics assembly mounted in the electronics compartment, wherein the electronics assembly includes an electrical connector.

Furthermore, the biostimulator can comprise an (or said) electrical feedthrough assembly, particularly according to the disclosure, mounted on the housing.

It is also possible that the electrical feedthrough assembly includes an electrode body including a cup having an electrode wall extending distally from an electrode base around an electrode cavity located on the longitudinal axis, and a pin extending proximally from the electrode base along the longitudinal axis into contact with the electrical connector of the electronics assembly, and that particularly the cup and the pin are integrally formed such that the electrode body is monolithic.

It can be possible that the electrical feedthrough assembly further includes: an insulator having an insulator wall extending distally from an insulator base around the electrode wall, wherein the insulator base is proximal to the electrode base, wherein an insulator hole extends through the insulator base along the longitudinal axis, and wherein the pin extends through the insulator hole from the electrode base to the electrical connector.

It can be possible that the electrical feedthrough assembly further includes a flange mounted on the housing and having a mounting wall extending around the insulator wall.

The bio stimulator can further comprise a helix mount mounted on the flange.

The biostimulator can further comprise a gasket having an annular body extending around the electrode wall, wherein the annular body is resiliently compressed between the helix mount and the mounting wall.

The biostimulator can further comprise a fixation element mounted on the helix mount, wherein the fixation element includes a helix revolving about the longitudinal axis in a first rotational direction, and wherein the helix mount is mounted on the flange by a threaded connection having threads revolving about the longitudinal axis in a second rotational direction opposite to the first rotational direction.

It can be possible that the electrical feedthrough assembly further comprises an electrode tip mounted on a distal end of the electrode body, wherein the electrode tip includes a tip hole extending through the electrode tip along the longitudinal axis from a distal tip end to a proximal tip end.

It can be possible that a first diameter of the tip hole at the distal tip end is less than a second diameter of the tip hole at the proximal tip end.

It can be possible that the electrical feedthrough assembly further comprises a filler in the electrode cavity, wherein the filler includes a therapeutic agent in a silicone matrix.

It can be possible that the electrical feedthrough assembly further comprises a retention feature within the electrode cavity that maintains the filler at a predetermined location within the electrode cavity.

It can be possible that the retention feature includes one or more protrusions extending from the electrode wall and in contact with an outer surface of the filler.

It can be possible that the one or more protrusions include a plurality of protrusions spaced equidistantly about the longitudinal axis.

It can be possible that the retention feature includes one or more tabs formed from the electrode wall and bent inwardly into the electrode cavity.

It can be possible that the retention feature includes a lip extending circumferentially about an interior surface of the electrode wall and into the electrode cavity.

It can be possible that the retention feature includes a coil disposed within the electrode cavity, wherein the coil extends along the longitudinal axis and is in contact with an outer surface of the filler.

It can be possible that the retention feature includes a spring disposed within the electrode cavity, wherein the spring extends along the longitudinal axis and is in contact with an outer surface of the filler.

It can be provided that the retention feature includes a spacer disposed within the electrode cavity, wherein the spacer includes a through hole extending along the longitudinal axis, the spacer being in contact with an outer surface of the filler.

It can be provided that the retention feature includes a tubular spacer disposed within the electrode cavity, wherein the tubular spacer includes a through hole extending along the longitudinal axis, the tubular spacer being in contact with an outer surface of the filler.

It can be provided that the retention feature includes a first retention feature and a second retention feature within the electrode cavity that maintain the filler at the predetermined location within the electrode cavity.

It can be provided that the first retention feature is integrally formed with the electrode wall and the second retention feature is inserted into the electrode cavity.

It can be provided that the first retention feature is a plurality of protrusions extending inwardly toward the longitudinal axis and the second retention feature is a coil inserted into the electrode cavity distal the filler.

Furthermore, it can be provided that the plurality of protrusions consists of three protrusions evenly distributed about the longitudinal axis.

It can be provided that the plurality of protrusions comprise three protrusions evenly distributed about the longitudinal axis.

It can be provided that that the plurality of protrusions comprise three dimples evenly distributed about the longitudinal axis.

It is also possible that the one or more retention features comprise a first retention feature, which consists of three protrusions evenly distributed about the longitudinal axis, and a second retention feature comprising a coil inserted into the electrode cavity distal the filler.

It is also possible that the one or more retention features comprise a first retention feature, which comprises of three dimples evenly distributed about the longitudinal axis, and a second retention feature comprising a coil inserted into the electrode cavity distal the filler.

According to another aspect of the disclosure a method is provided, particularly for manufacturing the electrical feedthrough assembly or the biostimulator according to the disclosure.

The method can comprise the following steps, carried out one after the other or in any order, whereby individual steps can also be repeated: Forming a distal portion of an electrode body, wherein the distal portion includes a cup having an electrode wall extending distally from an electrode base around an electrode cavity located on a longitudinal axis; Forming a proximal portion of the electrode body, wherein the proximal portion includes a pin that is integral to the cup, and wherein the pin extends proximally from the electrode base along the longitudinal axis.

The method can further comprise inserting the pin through an insulator hole of an insulator; and bonding the pin to the insulator by a braze joint.

The method can further comprise inserting the insulator into a mounting hole in a flange; and bonding the insulator to the flange by a second braze joint.

The method can further comprise inserting a filler in the electrode cavity such that the filler is placed in contact with a retention feature within the electrode cavity.

It can further be provided that the retention feature includes one or more protrusions extending from the electrode wall, the method further comprising forming the one or more protrusions.

It can also be provided that the retention feature includes a circumferential lip extending about the electrode wall, the method further comprising forming the circumferential lip.

It can also be provided that the retention feature includes one of more tabs cut from the electrode wall, the method further comprising forming the one or more tabs and pressing the one or more tabs inwardly toward the longitudinal axis.

It can also be provided that a retention feature of the one or more retention features is insertable into the electrode cavity, the method further comprising inserting the retention feature into the electrode cavity.

It can also be provided that the retention feature is a coil disposed within the electrode cavity and extending along the longitudinal axis, the method further comprising inserting the coil into the electrode cavity subsequent to inserting the filler.

It can also be provided that the retention feature is a spring disposed within the electrode cavity and extending along the longitudinal axis, the method further comprising inserting the spring into the electrode cavity subsequent to inserting the filler.

It can also be provided that the retention feature is a spacer disposed within the electrode cavity and extending along the longitudinal axis, the method further comprising inserting the spacer into the electrode cavity subsequent to inserting the filler.

It can also be provided that the retention feature is a tubular spacer disposed within the electrode cavity and extending along the longitudinal axis, the method further comprising inserting the tubular spacer into the electrode cavity subsequent to inserting the filler.

It can also be provided that the retention feature is integrally formed with the electrode wall and extends inwardly into the electrode cavity, the method further comprising forming the retention feature from the electrode wall.

It can also be provided that the retention feature is insertable into the electrode cavity, the method further comprising inserting the retention feature into the electrode cavity.

It can also be provided that the retention feature is a first retention feature and wherein inserting the filler into the electrode cavity further comprises inserting the filler into the electrode cavity such that the filler is placed into contact with a second retention feature within the electrode cavity.

It can also be provided that the first retention feature is integrally formed with the electrode wall and the second retention feature is insertable into the electrode cavity, the method further comprising: forming the first retention feature; and inserting the second retention feature into the electrode cavity.

The method can further comprise mounting an electrode tip on a distal end of the electrode body, wherein the electrode tip includes a tip hole extending through the electrode tip along the longitudinal axis from a distal tip end to a proximal tip end within the electrode cavity, and wherein a first diameter of the tip hole at the distal tip end is less than a second diameter of the tip hole at the proximal tip end.

According to another aspect of the disclosure, an electrical feedthrough assembly for a biostimulator can be provided.

The electrical feedthrough assembly can comprise an electrode body including an electrode wall extending distally from an electrode base around an electrode cavity located on a longitudinal axis.

The electrical feedthrough assembly can also comprise an electrode tip mounted on a distal end of the electrode body.

The electrical feedthrough assembly can also comprise a filler disposed within the electrode cavity.

The electrical feedthrough assembly can also comprise a retention feature disposed within the electrode cavity and in contact with an outer surface of the filler such that the filler is retained within the electrode cavity at a predetermined location offset from the electrode tip.

It can also be provided that the filler includes a therapeutic agent in a silicone matrix.

It can also be provided that the retention feature includes one or more protrusions extending from the electrode wall into the electrode cavity.

It can also be provided that the one or more protrusions include a plurality of protrusions spaced equidistantly about the longitudinal axis.

It can also be provided that the retention feature includes a spring having closed ends, the spring being disposed within the electrode cavity distal the filler and extending along the longitudinal axis.

It can also be provided that the spring has a length from and including about 0.05 inches to and including about 0.075 inches.

It can also be provided that the spring has a diameter from and including about 0.025 inches to and including about 0.050 inches.

It can also be provided that the spring has a pitch from and including about 0.005 inches to and including about 0.020 inches.

It can also be provided that the spring is formed from a wire having a diameter from and including about 0.0020 inches to and including about 0.0040 inches.

It can also be provided that the spring is formed from MP35N steel.

It can also be provided that the retention feature includes a coil having open ends, the coil disposed within the electrode cavity distal the filler and extending along the longitudinal axis.

It can also be provided that the coil has a length from and including about 0.020 inches to and including about 0.040 inches.

It can also be provided that the coil has a diameter from and including about 0.020 inches to and including about 0.050 inches.

It can also be provided that the coil has a pitch from and including about 0.020 inches to and including about 0.040 inches.

It can also be provided that the coil is formed from a wire having a diameter from and including about 0.004 inches to and including about 0.010 inches.

It can also be provided that the coil is formed from MP35N steel.

It can also be provided that the retention feature includes a spacer disposed within the electrode cavity distal the filler.

It can also be provided that the retention feature includes a tubular spacer disposed within the electrode cavity distal the filler. It can also be provided that the retention feature includes a plurality of legs extending proximally from the electrode tip.

It can also be provided that each of the plurality of legs extends parallel to the longitudinal axis.

It can also be provided that each of the plurality of legs extends at an angle relative to the longitudinal axis.

It can also be provided that the retention feature is a first retention feature, and the electrical feedthrough assembly further comprising a second retention feature.

It can also be provided that the first retention feature is integrally formed with the electrode wall and the second retention feature is inserted into the electrode cavity.

It can also be provided that the first retention feature includes one or more protrusions extending from the electrode wall into the electrode cavity and the second retention feature includes a coil having open ends, the coil disposed within the electrode cavity distal the filler and extending along the longitudinal axis.

It can also be provided that the one or more protrusions consists of three protrusions distributed evenly about the longitudinal axis.

It can also be provided that the retention feature proximally biases the filler toward the electrode base.

It can also be provided that the electrode body includes a cup including the electrode wall and the electrode base and a pin extending proximally from the electrode base along the longitudinal axis, wherein the cup and the pin are integrally formed such that the electrode body is monolithic.

According to another aspect of the disclosure, a biostimulator is provided.

The biostimulator can comprise a housing having a longitudinal axis and containing an electronics compartment.

Furthermore, the biostimulator can comprise an electronics assembly mounted in the electronics compartment, wherein the electronics assembly includes an electrical connector.

Furthermore, the biostimulator can comprise an (or said) electrical feedthrough assembly, particularly according to the disclosure, mounted on the housing.

Furthermore, the electrical feedthrough assembly can include at least one of the following: an electrode body including a cup having an electrode wall extending distally from an electrode base around an electrode cavity located on the longitudinal axis; an electrode tip mounted on a distal end of the electrode body; a filler disposed within the electrode cavity; and a retention feature disposed within the electrode cavity and in contact with an outer surface of the filler such that the filler is retained within the electrode cavity at a predetermined location offset from the electrode tip.

It is possible that the filler includes a therapeutic agent in a silicone matrix.

It is also possible that the retention feature includes one or more protrusions extending from the electrode wall into the electrode cavity.

It is also possible that the one or more protrusions include a plurality of protrusions spaced equidistantly about the longitudinal axis.

It is also possible that the retention feature includes a spring having closed ends, the spring being disposed within the electrode cavity distal the filler and extending along the longitudinal axis.

It is also possible that the retention feature includes a coil having open ends, the coil disposed within the electrode cavity distal the filler and extending along the longitudinal axis.

It is also possible that the retention feature includes a spacer, e.g. tubular spacer, disposed within the electrode cavity distal the filler.

It is also possible that the retention feature includes a plurality of legs extending proximally from the electrode tip.

It is also possible that each of the plurality of legs extends parallel to the longitudinal axis.

It is also possible that each of the plurality of legs extends at an angle relative to the longitudinal axis.

It is also possible that the retention feature is a first retention feature, the electrical feedthrough assembly further comprising a second retention feature.

It is also possible that the first retention feature is integrally formed with the electrode wall and the second retention feature is inserted into the electrode cavity.

It is also possible that the first retention feature includes one or more protrusions extending from the electrode wall into the electrode cavity and the second retention feature includes a coil having open ends, the coil disposed within the electrode cavity distal the filler and extending along the longitudinal axis.

It is also possible that the one or more protrusions consists of three protrusions distributed evenly about the longitudinal axis.

It is also possible that the retention feature proximally biases the filler.

It is also possible that the electrode body includes a cup including the electrode wall and the electrode base and a pin extending proximally from the electrode base along the longitudinal axis, wherein the cup and the pin are integrally formed such that the electrode body is monolithic.

According to another aspect of the disclosure, a method is provided, particularly for manufacturing the electrical feedthrough assembly or the biostimulator according to the disclosure, comprising at least one of the following steps, which may be carried out one after another or in any order, wherein single steps can also be repeated:

According to one step, the method can comprise obtaining an electrode body including a distal portion, the distal portion including an electrode wall extending distally from an electrode base around an electrode cavity located on a longitudinal axis.

According to another step, the method can comprise inserting a filler in the electrode cavity such that an outer surface of the filler is placed in contact with a retention feature within the electrode cavity to maintain the filler at a predetermined location within the electrode cavity.

According to another step, the method can comprise coupling an electrode distal tip end to a distal end of the electrode body such that the filler is contained within the electrode cavity at the predetermined location.

It can be provided that the retention feature is integrally formed with the electrode wall and extends into the electrode cavity toward the longitudinal axis, the method further comprising forming the retention feature.

It can be provided that the retention feature includes one or more protrusions and forming the retention feature comprises indenting an exterior surface of the electrode wall.

It can be provided that the retention feature includes dimples and forming the dimples comprises punching indentations into an exterior surface of the electrode wall.

It can be provided that the retention feature includes one or more tabs and forming the retention feature comprises cutting each of the one or more tabs from the electrode wall and pressing the tabs inwardly toward the longitudinal axis.

It can be provided that the retention feature is a lip extending circumferentially about the electrode wall and forming the lip comprises indenting an exterior surface of the electrode wall to form the lip.

It can be provided that the retention feature is insertable into the electrode cavity, the method further comprising inserting the retention feature into the electrode cavity.

It can be provided that the retention feature is a coil having open ends and inserting the retention feature into the electrode cavity comprises inserting the coil such that the coil extends along the longitudinal axis.

It can be provided that the retention feature is a spring having closed ends and inserting the retention feature into the electrode cavity comprises inserting the spring such that the spring extends along the longitudinal axis.

It can be provided that the retention feature is a spacer and inserting the retention feature into the electrode cavity comprises inserting the spacer such that the spacer extends along the longitudinal axis.

It can be provided that the retention feature is a tubular spacer and inserting the retention feature into the electrode cavity comprises inserting the tubular spacer such that the tubular spacer extends along the longitudinal axis.

It can be provided that the retention feature is a first retention feature, the method further comprising inserting the filler in the electrode cavity such that the outer surface of the filler is placed in contact with a second retention feature within the electrode cavity.

It can be provided that the first retention feature is integrally formed with the electrode wall and the second retention feature is insertable into the electrode cavity, the method further comprising: forming the first retention feature; and inserting the second retention feature into the electrode cavity.

It can be provided that the first retention feature includes one or more protrusions and forming the first retention feature comprises indenting an exterior surface of the electrode wall.

It can be provided that the second retention feature is a coil having open ends and inserting the retention feature into the electrode cavity comprises inserting the coil such that the coil extends along the longitudinal axis.

A biostimulator according to the disclosure can particularly be configured as a leadless biostimulator, e.g., a leadless cardiac pacemaker. The biostimulator can also include a housing having pacing electrodes. For example, the biostimulator includes each of a distal electrode and a proximal electrode disposed on or integrated into the housing. The electrodes can be integral to the housing or connected to the housing, e.g., at a distance of less than several centimeters from the housing. The housing can contain an energy source to provide power to the pacing electrodes. The energy source can be, for example, a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. According to one implementation, the energy source can be an energy harvesting device, such as a piezoelectric device that converts mechanical strain into electrical current or voltage. The energy source can also be an ultrasound transmitter that uses ultrasound technology to transfer energy from an ultrasound subcutaneous pulse generator to a receiver-electrode implanted on an endocardial wall.

The housing can have a longitudinal axis, which may be an axis of symmetry along which several other biostimulator components are disposed. For example, an electrical feedthrough assembly (particularly according to the disclosure) can be mounted on a distal end of the housing along the longitudinal axis. Similarly, a feature to facilitate fixation of the biostimulator may be mounted on the electrical feedthrough assembly. For example, the biostimulator includes a helix mount mounted on the electrical feedthrough assembly around the longitudinal axis. In one implementation, a fixation element can be mounted on the helix mount along the longitudinal axis.

The electrical feedthrough assembly can be an unfiltered assembly. More particularly, the configuration of the electrical feedthrough assembly can include an active component, e.g., the distal electrode, isolated from a ground component (e.g., a flange) by an insulator. The electrical feedthrough assembly for the biostimulator can include the distal electrode, which may further include an electrode body and/or an electrode tip. The electrode tip may be mounted on the electrode body, e.g., on a distal end of the electrode body.

The biostimulator, and more particularly the electrical feedthrough assembly, can include a filler, such as a monolithic controlled release device (MCRD). The filler may include a therapeutic material, and can be loaded into the cup. Accordingly, the filler can deliver a specified dose of a therapeutic agent, e.g., a corticosteroid, into target tissue at an implantation site of the biostimulator within a patient.

According to an alternative implementation of an electrode body in accordance with the present disclosure is provided that includes various protrusions to retain a filler within an electrode cavity defined within the electrode body. The protrusions can be tabs that are bent inward from the electrode wall toward a longitudinal axis of the electrode body. For example, the electrode wall can have a laser cut trench or slot that extends around the tab. The tab can then be pressed inward to bend about a tab base. More particularly, the tab can extend from the tab base to a tab tip. When the tab is bent inward, the tab tip can be radially inward of the electrode wall, and thus, may be placed in contact with the filler to retain the filler within the electrode cavity.

In one aspect of the present disclosure an electrical feedthrough assembly for a biostimulator is provided. The feedthrough assembly includes an electrode body including a cup having an electrode wall extending distally from an electrode base around an electrode cavity located on a longitudinal axis. The feedthrough assembly further includes a pin extending proximally from the electrode base along the longitudinal axis, wherein the cup and the pin are integrally formed such that the electrode body is monolithic.

In certain implementations, the electrical feedthrough assembly further includes an insulator having an insulator wall extending distally from an insulator base around the electrode wall such that the insulator base is proximal to the electrode base. An insulator hole extends through the insulator base along the longitudinal axis and the pin extends through the insulator hole from the electrode base to a proximal end of the electrode body. The feedthrough assembly further includes a flange having a mounting wall extending around the insulator wall. In such implementations, the electrical feedthrough assembly may further include a gasket having an annular body extending around the electrode wall, the gasket being distal to the insulator wall and the mounting wall and including a resilient material.

In other implementations, the electrical feedthrough assembly further includes an electrode tip mounted on a distal end of the electrode body. The electrode tip includes a tip hole extending through the electrode tip along the longitudinal axis from a distal tip end to a proximal tip end. In such implementations, a first diameter of the tip hole at the distal tip end may be less than a second diameter of the tip hole at the proximal tip end. In other implementations, a weeping hole may extend through one or more of the electrode wall or the electrode tip along a transverse axis orthogonal to the longitudinal axis.

In still other implementations, the electrical feedthrough assembly may further include a filler in the electrode cavity, the filler including a therapeutic agent in a silicone matrix. In such implementations, the electrical feedthrough assembly may further include a retention feature within the electrode cavity that maintains the filler at a predetermined location within the electrode cavity. The retention feature may include one or more protrusions extending from the electrode wall and in contact with an outer surface of the filler. The one or more protrusions may include a plurality of protrusions spaced equidistantly about the longitudinal axis. As another example, the retention feature may include one or more tabs formed from the electrode wall and bent inwardly into the electrode cavity. As yet another example, the retention feature may include a lip extending circumferentially about an interior surface of the electrode wall and into the electrode cavity.

The retention feature may also be disposed within the electrode cavity. For example, in one implementation, the retention feature may include a coil disposed within the electrode cavity, and extending along the longitudinal axis to be in contact with an outer surface of the filler. In another example, the retention feature may include a spring disposed within the electrode cavity, extending along the longitudinal axis, and in contact with an outer surface of the filler. In yet another example, the retention feature may include a spacer, which may be, for example, a tubular or hexagonal spacer, disposed within the electrode cavity, the tubular spacer including a through hole extending along the longitudinal axis.

In certain implementations, the retention feature may be a first retention feature and the electrical feedthrough assembly may further include a second retention feature within the electrode cavity that maintains the filler at the predetermined location within the electrode cavity. In such implementations, the first retention feature may be integrally formed with the electrode wall and the second retention feature may be inserted into the electrode cavity. For example, the first retention feature may include a plurality of protrusions extending inwardly toward the longitudinal axis and the second retention feature may be a coil inserted into the electrode cavity distal the filler. The plurality of protrusions may consist of three protrusions evenly distributed about the longitudinal axis.

In another aspect of the present disclosure, a biostimulator is provided. The biostimulator includes a housing having a longitudinal axis and containing an electronics compartment and an electronics assembly mounted in the electronics compartment, the electronics assembly including an electrical connector. The biostimulator further includes an electrical feedthrough assembly mounted on the housing. The electrical feedthrough assembly includes an electrode body including a cup having an electrode wall extending distally from an electrode base around an electrode cavity located on the longitudinal axis. The electrical feedthrough assembly further includes a pin extending proximally from the electrode base along the longitudinal axis into contact with the electrical connector of the electronics assembly. The cup and the pin are integrally formed such that the electrode body is monolithic.

In one implementation, the electrical feedthrough assembly further includes an insulator having an insulator wall extending distally from an insulator base around the electrode wall. The insulator base is proximal to the electrode base and an insulator hole extends through the insulator base along the longitudinal axis. The pin extends through the insulator hole from the electrode base to the electrical connector. In such implementations, the electrical feedthrough assembly further includes a flange mounted on the housing and having a mounting wall extending around the insulator wall. In such implementations, the biostimulator may further include a helix mount mounted on the flange and a gasket having an annular body extending around the electrode wall such that the annular body is resiliently compressed between the helix mount and the mounting wall. The helix mount may include a fixation element mounted on the helix mount. The fixation element may include a helix revolving about the longitudinal axis in a first rotational direction and the helix mount may be mounted on the flange by a threaded connection having threads revolving about the longitudinal axis in a second rotational direction opposite to the first rotational direction.

In another implementation the electrical feedthrough assembly of the biostimulator further includes an electrode tip mounted on a distal end of the electrode body, the electrode tip including a tip hole extending through the electrode tip along the longitudinal axis from a distal tip end to a proximal tip end. In such implementations, a first diameter of the tip hole at the distal tip end may be less than a second diameter of the tip hole at the proximal tip end.

In yet another implementation, the electrical feedthrough assembly of the bio stimulator may include a filler in the electrode cavity, the filler including a therapeutic agent in a silicone matrix. In such implementations, the electrical feedthrough assembly may further include a retention feature within the electrode cavity that maintains the filler at a predetermined location within the electrode cavity. In one example, the retention feature may include one or more protrusions extending from the electrode wall and in contact with an outer surface of the filler and the one or more protrusions may include a plurality of protrusions spaced equidistantly about the longitudinal axis. In another example, the retention feature may include one or more tabs formed from the electrode wall and bent inwardly into the electrode cavity. In yet another example, the retention feature may include a lip extending circumferentially about an interior surface of the electrode wall and into the electrode cavity. In still another example, the retention feature may include a coil disposed within the electrode cavity, the coil extending along the longitudinal axis and in contact with an outer surface of the filler. In yet another example, the retention feature may include a spring disposed within the electrode cavity, the spring extending along the longitudinal axis and in contact with an outer surface of the filler. In another example, the retention feature may include a tubular spacer disposed within the electrode cavity, the tubular spacer including a through hole extending along the longitudinal axis.

The retention feature may be a first retention feature and the electrical feedthrough may further include a second retention feature within the electrode cavity that maintains the filler at the predetermined location within the electrode cavity. In such implementations, the first retention feature may be integrally formed with the electrode wall and the second retention feature may be inserted into the electrode cavity. For example, the first retention feature may include a plurality of protrusions extending inwardly toward the longitudinal axis (e.g., three protrusions evenly distributed about the longitudinal axis) and the second retention feature may be a coil inserted into the electrode cavity distal the filler.

In another aspect of the present disclosure a method is provided that includes forming a distal portion of an electrode body and forming a proximal portion of the electrode body. The distal portion includes a cup having an electrode wall extending distally from an electrode base around an electrode cavity located on a longitudinal axis. The proximal portion includes a pin that is integral to the cup such that the pin extends proximally from the electrode base along the longitudinal axis.

In one implementation, the method further includes inserting the pin through an insulator hole of an insulator and bonding the pin to the insulator by a braze joint. The method may further include inserting the insulator into a mounting hole in a flange and bonding the insulator to the flange by a second braze joint. The method may also include inserting a filler in the electrode cavity such that the filler is placed in contact with a retention feature within the electrode cavity.

In one implementation, the retention feature may include one or more protrusions extending from the electrode wall and the method may further include forming the one or more protrusions. In another implementation, the retention feature may include a circumferential lip extending about the electrode wall and the method may further include forming the circumferential lip. In still another implementation, the retention feature may include one of more tabs cut from the electrode wall and the method may further including forming the one or more tabs and pressing the one or more tabs inwardly toward the longitudinal axis. In yet another implementation, the retention feature of the one or more retention features is insertable into the electrode cavity and the method may further include inserting the retention feature into the electrode cavity. For example, the retention feature may be a coil disposed within the electrode cavity and extending along the longitudinal axis and the method may further including inserting the coil into the electrode cavity subsequent to inserting the filler. In another example, the retention feature may be a spring disposed within the electrode cavity and extending along the longitudinal axis and the method further may further include inserting the spring into the electrode cavity subsequent to inserting the filler. In yet another example, the retention feature may be a tubular spacer disposed within the electrode cavity and extending along the longitudinal axis and the method may further include inserting the tubular spacer into the electrode cavity subsequent to inserting the filler.

In another implementation, the retention feature is integrally formed with the electrode wall and extends inwardly into the electrode cavity and the method further includes forming the retention feature from the electrode wall. In still another implementation, the retention feature is insertable into the electrode cavity and the method further includes inserting the retention feature into the electrode cavity.

In yet another implementation, the retention feature is a first retention feature and inserting the filler into the electrode cavity further includes inserting the filler into the electrode cavity such that the filler is placed into contact with a second retention feature within the electrode cavity. In such implementations, the first retention feature may be integrally formed with the electrode wall and the second retention feature may be insertable into the electrode cavity. In such cases, the method may further include forming the first retention feature and inserting the second retention feature into the electrode cavity.

In still another implementation, the method may further include mounting an electrode tip on a distal end of the electrode body. The electrode tip may include a tip hole extending through the electrode tip along the longitudinal axis from a distal tip end to a proximal tip end within the electrode cavity, and a first diameter of the tip hole at the distal tip end may be less than a second diameter of the tip hole at the proximal tip end.

In yet another aspect of the present disclosure, an electrical feedthrough assembly for a biostimulator is provided. The electrical feedthrough assembly includes an electrode body including an electrode wall extending distally from an electrode base around an electrode cavity located on a longitudinal axis, an electrode tip mounted on a distal end of the electrode body, a filler disposed within the electrode cavity and a retention feature disposed within the electrode cavity. The retention feature is in contact with an outer surface of the filler such that the filler is retained within the electrode cavity at a predetermined location offset from the electrode tip. The filler may include, for example, a therapeutic agent in a silicone matrix.

In one implementation, the retention feature includes one or more protrusions extending from the electrode wall into the electrode cavity. For example, the one or more protrusions may include a plurality of protrusions spaced equidistantly about the longitudinal axis.

In another implementation, the retention feature includes a spring having closed ends, the spring being disposed within the electrode cavity distal the filler and extending along the longitudinal axis. Although the specific characteristics of the spring may vary, in at least certain implementations, the spring may have at least one of a length from and including about 0.05 inches to and including about 0.075 inches, a diameter from and including about 0.025 inches to and including about 0.050 inches, and/or a pitch from and including about 0.005 inches to and including about 0.020 inches. The spring may also be formed from a wire having a diameter from and including about 0.0020 inches to and including about 0.0040 inches and the wire may be formed from MP35N steel.

In another implementation, the retention feature includes a coil having open ends, the coil disposed within the electrode cavity distal the filler and extending along the longitudinal axis. Although the specific characteristics of the spring may vary, in at least certain implementations, the coil may have at least one of a length from and including about 0.020 inches to and including about 0.040 inches, a diameter from and including about 0.020 inches to and including about 0.050 inches, and/or a pitch from and including about 0.020 inches to and including about 0.040 inches. The coil may also be formed from a wire having a diameter from and including about 0.004 inches to and including about 0.010 inches and the wire may be formed from MP35N steel.

In certain implementations, a spring, coil, and/or spacer block the filler from dislodging from the cup. For example, the filler can have a filler dimension, e.g., a maximum cross-sectional dimension taken transverse to the longitudinal axis, that is greater than an inner dimension of the spring, coil, and/or spacer e.g., an inner diameter of the coil or spring or the inner diameter of the through hole of the spacer. Such a relative size prevents the filler from passing through the inner diameter of the coil, spring and/or spacer, and thus, promotes retention of the filler within the cup. Furthermore, the inner dimension of the spring, coil, or spacer can be sized to allow a maximum area of the filler to be exposed to a surrounding environment through the interior space of the coil or spring. Accordingly, drug can consistently elute from the filler through the coil, spring, or spacer toward the target tissue for reliable and predictable therapy.

In yet another implementation, the retention feature includes a tubular spacer disposed within the electrode cavity distal the filler.

In yet another implementation, the retention feature includes a hexagonal spacer disposed within the electrode cavity distal the filler.

In another implementation, the retention feature includes a plurality of legs extending proximally from the electrode tip. In such implementations, each of the plurality of legs may extend parallel to the longitudinal axis. Alternatively, each of the plurality of legs may extend at an angle relative to the longitudinal axis.

In certain implementations, the retention feature is a first retention feature and the electrical feedthrough assembly further includes a second retention feature. In such implementations, the first retention feature may be integrally formed with the electrode wall and the second retention feature may be inserted into the electrode cavity. For example, the first retention feature may include one or more protrusions extending from the electrode wall into the electrode cavity (e.g., three protrusions distributed evenly about the longitudinal axis) and the second retention feature may include a coil having open ends, the coil being disposed within the electrode cavity distal the filler and extending along the longitudinal axis.

In still other implementations, the retention feature proximally biases the filler toward the electrode base and away from the electrode tip.

In other implementations, the electrode body includes a cup including the electrode wall and the electrode base and a pin extending proximally from the electrode base along the longitudinal axis, wherein the cup and the pin are integrally formed such that the electrode body is monolithic.

In still another aspect of the present disclosure, a biostimulator is provided. The biostimulator includes a housing having a longitudinal axis and containing an electronics compartment and an electronics assembly mounted in the electronics compartment, the electronics assembly including an electrical connector. The biostimulator further includes an electrical feedthrough assembly mounted on the housing. The electrical feedthrough assembly includes an electrode body including a cup having an electrode wall extending distally from an electrode base around an electrode cavity located on the longitudinal axis, an electrode tip mounted on a distal end of the electrode body, and a filler disposed within the electrode cavity. The electrical feedthrough assembly further includes a retention feature disposed within the electrode cavity and in contact with an outer surface of the filler such that the filler is retained within the electrode cavity at a predetermined location offset from the electrode tip.

In certain implementations, the filler includes a therapeutic agent in a silicone matrix.

The retention feature may take various forms in implementations of the present disclosure. For example, the retention feature may include one or more protrusions extending from the electrode wall into the electrode cavity. In such cases, the one or more protrusions may include a plurality of protrusions spaced equidistantly about the longitudinal axis. In another example, the retention feature may include a spring having closed ends, the spring being disposed within the electrode cavity distal the filler and extending along the longitudinal axis. In yet another example, the retention feature may include a coil having open ends, the coil being disposed within the electrode cavity distal the filler and extending along the longitudinal axis. In still another example, the retention feature may include a tubular spacer disposed within the electrode cavity distal the filler. In another example, the retention feature includes a plurality of legs extending proximally from the electrode tip. In such cases, the plurality of legs may extend parallel to the longitudinal axis or at an angle relative to the longitudinal axis.

In certain implementations, the retention feature is a first retention feature and the electrical feedthrough assembly further includes a second retention feature. In such implementations, the first retention feature may be integrally formed with the electrode wall and the second retention feature may be inserted into the electrode cavity. For example, the first retention feature may include one or more protrusions (e.g., three protrusions distributed evenly about the longitudinal axis) extending from the electrode wall into the electrode cavity and the second retention feature may include a coil having open ends, the coil being disposed within the electrode cavity distal the filler and extending along the longitudinal axis.

In still other implementations the retention feature proximally biases the filler.

In other implementations, the electrode body includes a cup including the electrode wall and the electrode base and a pin extending proximally from the electrode base along the longitudinal axis, wherein the cup and the pin are integrally formed such that the electrode body is monolithic.

In another aspect of the present disclosure, a method is provided. The method includes obtaining an electrode body including a distal portion, the distal portion including an electrode wall extending distally from an electrode base around an electrode cavity located on a longitudinal axis. The method further includes inserting a filler in the electrode cavity such that an outer surface of the filler is placed in contact with a retention feature within the electrode cavity to maintain the filler at a predetermined location within the electrode cavity. The method also includes coupling a distal electrode tip to a distal end of the electrode body such that the filler is contained within the electrode cavity at the predetermined location.

In certain implementations, wherein the retention feature is integrally formed with the electrode wall and extends into the electrode cavity toward the longitudinal axis and the method further includes forming the retention feature. In such implementations, the retention feature may include one or more protrusions and forming the retention feature may include indenting an exterior surface of the electrode wall. In another such implementation the retention feature may include one or more tabs and forming the retention feature may include cutting each of the one or more tabs from the electrode wall and pressing the tabs inwardly toward the longitudinal axis. In still another such implementation, the retention feature may be a lip extending circumferentially about the electrode wall and forming the lip may include indenting an exterior surface of the electrode wall to form the lip.

In other implementations, the retention feature is insertable into the electrode cavity and the method further includes inserting the retention feature into the electrode cavity. In one such implementation, the retention feature may be a coil having open ends and inserting the retention feature into the electrode cavity may include inserting the coil such that the coil extends along the longitudinal axis. In another such implementation, the retention feature may be a spring having closed ends and inserting the retention feature into the electrode cavity may include inserting the spring such that the spring extends along the longitudinal axis. In yet another such implementation, the retention feature may be a tubular spacer and inserting the retention feature into the electrode cavity may include inserting the tubular spacer such that the tubular spacer extends along the longitudinal axis.

In another implementation, the retention feature is a first retention feature and the method further includes inserting the filler in the electrode cavity such that the outer surface of the filler is placed in contact with a second retention feature within the electrode cavity. In such implementations, the first retention feature may be integrally formed with the electrode wall and the second retention feature may be insertable into the electrode cavity. In such cases, the method may further include forming the first retention feature and inserting the second retention feature into the electrode cavity. In one example, the first retention feature may include one or more protrusions and forming the first retention feature may include indenting an exterior surface of the electrode wall. As another example, the second retention feature may be a coil having open ends and inserting the retention feature into the electrode cavity may include inserting the coil such that the coil extends along the longitudinal axis.

The above summary does not include an exhaustive list of all aspects of the present disclosure. It is contemplated that implementations of the present disclosure include all systems and methods that can be practiced from all suitable combinations of the various aspects summarized above, as well as those disclosed in the Detailed Description below and particularly pointed out in the claims filed with this disclosure. Such combinations have particular advantages not specifically recited in the above summary.

BRIEF DESCRIPTION OF THE DRAWINGS

The novel features of implementations of the present disclosure are set forth with particularity in the claims that follow. A better understanding of the features and advantages of such implementations will be obtained by reference to the following detailed description that sets forth illustrative examples in which the principles of the disclosure are utilized, and the accompanying drawings of which:

DETAILED DESCRIPTION

Figure 1:
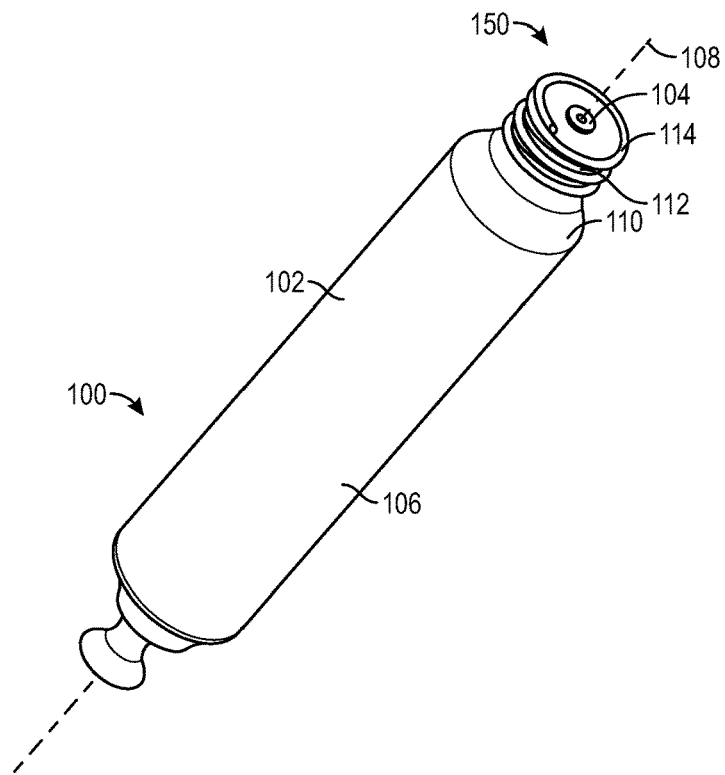
FIG. 1 is a perspective view of a bio stimulator, in accordance with an implementation of the present disclosure.

Implementations of the present disclosure include a biostimulator, e.g., a leadless cardiac pacemaker, having an electrical feedthrough that includes a monolithic electrode body having an electrode pin integral with an electrode cup. The pin and cup can transmit a pacing impulse from an electronics assembly to a target tissue without passing the pacing impulse through a weld, seam, etc. The biostimulator may be used to pace cardiac tissue as described below. The biostimulator may be used in other applications, however, such as deep brain stimulation. Thus, reference to the biostimulator as being a cardiac pacemaker is not limiting.

Implementations of the present disclosure may also include a biostimulator having an electrode within which a filler is disposed. The filler may be, for example, a monolithic controlled release device (MCRD) for delivering a therapeutic agent to an implantation site of the bio stimulator. To promote fluid exchange within the electrode cavity and sufficient exposure of the outer surface of the filler, the electrode may include various retention features configured to maintain the filler at an offset relative to one or more fluid ports of the electrode. Examples of such retention features include, without limitation, protrusions extending inwardly from a wall of the cavity into contact with the outer surface of the filler; a spring, coil, spacer, or similar component inserted into the electrode cavity; and/or proximally extending legs of a distal electrode tip component of the electrode.

Descriptions of various implementations of the present disclosure are made with reference to the figures. However, certain implementations may be practiced without one or more of these specific details, or in combination with other known methods and configurations. In the following description, numerous specific details are set forth, such as specific configurations, dimensions, and processes, in order to provide a thorough understanding of the example implementations. In other instances, well-known processes and manufacturing techniques have not been described in particular detail in order to not unnecessarily obscure the description. Reference throughout this specification to "one implementation," "an implementation," or the like, means that a particular feature, structure, configuration, or characteristic described is included in at least one implementation. Thus, the appearance of the phrase "one implementation," "an implementation," or the like, in various places throughout this specification are not necessarily referring to the same implementation. Furthermore, the particular features, structures, configurations, or characteristics may be combined in any suitable manner in one or more implementations.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various implementations below.

In one aspect of the present disclosure, a biostimulator is provided. The biostimulator includes an electrode body for delivering a pacing impulse to a target tissue. The electrode body can be monolithically formed, such that there are no welds, seams, burnishes, etc., as remnants of the manufacturing process. For example, the electrode body can have a cup and a pin portion that are integrally formed with each other in a machining process. The monolithic electrode body can provide several benefits, including more consistent transmission of the pacing impulse, a reduced likelihood of failure due to chemical or fluid ingress through the body, and an electrode surface morphology that is easier to clean, and thus, less likely to introduce contaminants into the target anatomy.

Referring to FIG. 1, a perspective view of a biostimulator 100 is shown in accordance with one implementation of the present disclosure. The biostimulator 100 can be a leadless biostimulator, e.g., a leadless cardiac pacemaker. The biostimulator 100 can include a housing 102 having pacing electrodes. For example, the biostimulator 100 includes each of a distal electrode 104 and a proximal electrode 106 disposed on or integrated into the housing 102. The electrodes 104, 106 can be integral to the housing 102 or connected to the housing 102, e.g., at a distance of less than several centimeters from the housing 102. The housing 102 can contain an energy source (not shown) to provide power to the pacing electrodes. The energy source can be, for example, a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In one implementation, the energy source can be an energy harvesting device, such as a piezoelectric device that converts mechanical strain into electrical current or voltage. The energy source can also be an ultrasound transmitter that uses ultrasound technology to transfer energy from an ultrasound subcutaneous pulse generator to a receiver-electrode implanted on an endocardial wall.

The housing 102 can have a longitudinal axis 108, which may be an axis of symmetry along which several other biostimulator components are disposed. For example, an electrical feedthrough assembly 110 can be mounted on a distal end of the housing 102 along the longitudinal axis 108. Similarly, a feature to facilitate fixation of the bio stimulator 100 may be mounted on the electrical feedthrough assembly 110. For example, the biostimulator 100 includes a helix mount 112 mounted on the electrical feedthrough assembly 110 around the longitudinal axis 108. In one implementation, a fixation element 114 is mounted on the helix mount 112 along the longitudinal axis 108. As illustrated in FIG. 1, the fixation element 114 may be a helical coil or wire; however, implementations of the present disclosure may include any suitable fixation element or elements. The assembled components of the biostimulator 100 can provide a distal region 150 that attaches to a target tissue, e.g., via engagement of the fixation element 114 with the target tissue. The distal region can deliver a pacing impulse to the target tissue, e.g., via the distal electrode 104 that is held against the target tissue.

Figure 2:
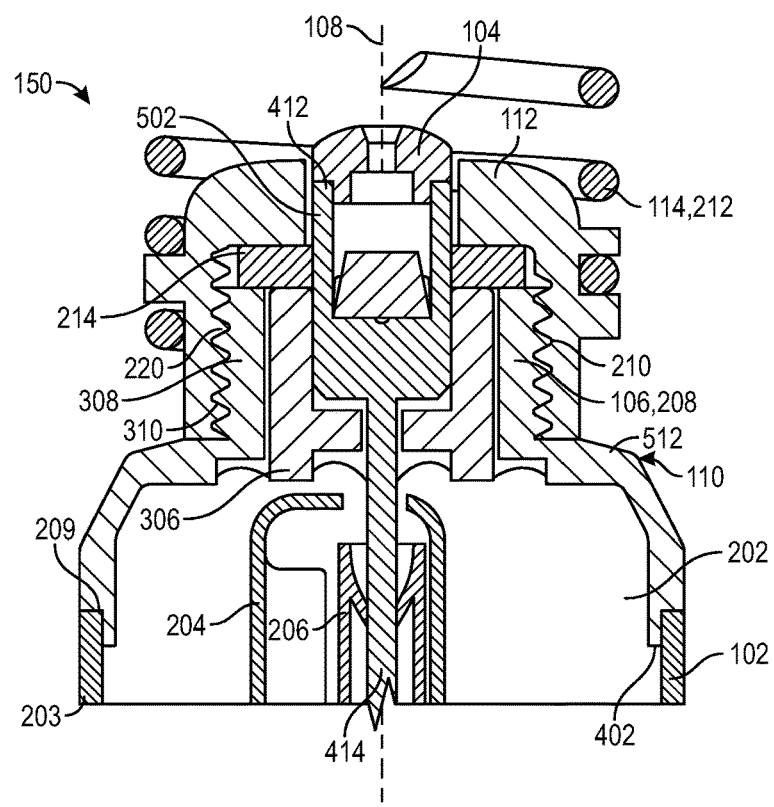
FIG. 2 is a longitudinal sectional view of a distal region of the bio stimulator of FIG. 1.

Referring to FIG. 2, a longitudinal sectional view of the distal region 150 of the biostimulator 100 of FIG. 1 is provided. The housing 102 can define an electronics compartment 202. More particularly, the electronics compartment 202 can be laterally surrounded by a housing wall 203, e.g., a cylindrical wall, extending around the longitudinal axis 108. The housing wall 203 can include a conductive, biocompatible, inert, and anodically safe material such as titanium, 316L stainless steel, or other similar materials, to laterally enclose the electronics compartment 202. Similarly, the electrical feedthrough assembly 110 can distally enclose the electronics compartment 202, and a power source container (not shown) can proximally enclose the electronics compartment 202. More particularly, the electronics feedthrough assembly 110, the housing wall 203, and the power source container, can surround a volume of the electronics compartment 202.

In one implementation, an electronics assembly 204 is mounted in the electronics compartment 202. The electronics assembly 204 can include, without limitation, a flexible circuit or a printed circuit board having one or more electronic components mounted on a substrate. For example, the electronics assembly 204 can include one or more processors, capacitors, etc., interconnected by electrical traces, vias, or other electrical connectors. In one implementation, the electronics assembly 204 includes an electrical connector 206 to connect to the electrical feedthrough assembly 110. For example, the electrical connector 206 can be a socket connector to receive an electrode pin 414, which is further illustrated and described in the context of FIG. 5, below.

Still referring to FIG. 2, the helix mount 112 can be mounted on the electrical feedthrough assembly 110. For example, the electrical feedthrough assembly 110 can include a flange 208 having a mounting wall 308 and a shoulder 512 (as further described in detail in the context of FIGS. 3 and 5, respectively), to receive the helix mount 112. In one implementation, the flange 208 is formed from titanium. The flange 208 can be mounted on the housing 102 and connected to the housing by a hermetic seal, e.g., a weld 209 or any other similar hermetically sealed connection. For example, the hermetic weld 209 can be formed circumferentially around a seam between a proximal end of the flange 208 and a distal end of the housing 102. In one implementation, the helix mount 112 is mounted on the flange 208 by a threaded connection 210. For example, the flange 208 can have an external thread 310 that mates with an internal thread 220 of the helix mount 112. Accordingly, the helix mount 112 can be screwed onto the mounting wall 308 of the flange 208. Alternatively, the helix mount 112 can be press fit onto the mounting wall 308, the helix mount 112 can be bonded to the mounting wall 308 by a thermal or adhesive bond, or the helix mount 112 and the electrical feedthrough assembly 110 can be joined in another manner, such as swaging.

In one implementation, the fixation element 114 includes a helix 212 mounted on the helix mount 112. The helix 212 can extend distally from the helix mount 112 about the longitudinal axis 108. For example, the helix 212 can revolve about the longitudinal axis 108. The helix 212 can include a spiral wire, formed by coiling or cut from a wall of a length of tubing, which extends in a rotational direction around the longitudinal axis 108. For example, the helix 212 can revolve in a right-handed direction about the longitudinal axis 108.

The helix 212 can be suitable for attaching the biostimulator 100 to tissue, such as heart tissue. For example, in the case of a right-handed spiral direction, the biostimulator 100 can be advanced into contact with a target tissue, and the biostimulator 100 can then be rotated in the right-handed direction to screw the helix 212 into the tissue. In one implementation, the rotational direction of the helix 212 is opposite to a rotational direction of the threaded connection 210 between the mounting wall 308 of the flange 208 and the helix mount 112. For example, the external thread 310 on the mounting wall 308 of the flange 208 may be left-handed, as compared to the right-handed direction of the helix 212. The threads 220, 310 of the threaded connection 210 therefore revolve about the longitudinal axis 108 in an opposite direction from the helix 212. Accordingly, when the helix 212 is screwed into the target tissue, the torque transmitted from the flange 208 to the helix mount 112 will be in a same direction as the threads 220, 310 of the threaded connection 210, and thus, the implantation torque will tend to tighten (rather than loosen) the threaded connection 210 between the electrical feedthrough assembly 110 and the fixation assembly 112 of the bio stimulator 100.

The biostimulator 100 can be implanted in a body region having fluids, e.g., within the blood of a heart chamber, and thus, portions of the bio stimulator 100 can be sealed and/or protected against fluid ingress that may compromise functionality of the biostimulator 100. For example, portions of the electrical feedthrough assembly 110, such as the flange 208, may be coated with a protective coating to prevent short circuiting of the distal electrode 104 and the proximal electrode 106. In one implementation, the distal electrode 104 is spatially near the flange 208, which can be a portion of the proximal electrode 106. Thus, if blood were allowed to fill the gap between the distal electrode 104 and the proximal electrode 106, the electrodes 104, 106 could be electrically shorted and pacing impulses may not properly pace the cardiac tissue. Accordingly, a barrier can be included in the biostimulator 100 to prevent blood from filling a cavity within the biostimulator between the distal electrode 104 and the proximal electrode 106.

In one implementation, a gasket 214 is resiliently compressed between the helix mount 112 and the mounting wall 308 of the flange 208. For example, the gasket 214 can have an annular body, e.g., an o-ring shape, which extends around a lateral wall of the distal electrode 104. As described below in the context of FIGS. 4 and 5, the lateral wall can be an electrode wall 502 of a cup portion 412 of the distal electrode 104. In one specific implementation, the gasket 214 can fill a gap between a proximal surface of the helix mount 112 and a distal face or surface of the electrical feedthrough assembly 110. For example, the gasket 214 can be distal to a wall of an insulator 306 (described below in further detail in the context of FIG. 3) and/or a face/surface of the flange 208. The gasket 214 can be formed at least in part from a resilient material, e.g., silicone, and thus, can be squeezed and deformed between the helix mount 112 and the electrical feedthrough assembly 110. The compressed gasket 214 can form a seal against the compressing surfaces to fill the gap between the distal electrode 104 and the proximal electrode 106. Accordingly, the gasket 214 can separate and protect the conductive surfaces of the biostimulator 100 from short circuiting.

Figure 3:
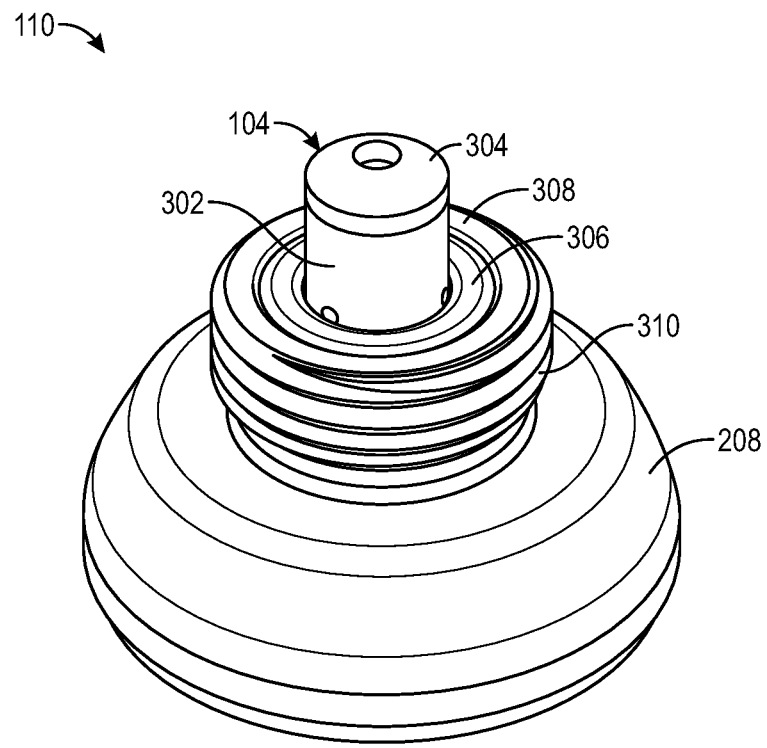
FIG. 3 is a perspective view of an electrical feedthrough assembly of the biostimulator of FIG. 1.

Referring to FIG. 3, a perspective view of the electrical feedthrough assembly 110 of the biostimulator 100 of FIGS. 1 and 2 is illustrated. The electrical feedthrough assembly 110 can be a multifunction component. For example, unlike a traditional pacemaker where the electrical feedthrough is separated from the pacing site by a lead, the distal electrode 104 of the electrical feedthrough assembly 110 of the bio stimulator 100 may be in direct contact with the stimulation site. Accordingly, the electrical feedthrough assembly 110 can not only serve as the electrical pass-through from a hermetic package to a surrounding environment, but may also serve other functions, such as providing a housing for a steroid or other filler and direct tissue interaction, as described below.

In certain implementations, the electrical feedthrough assembly 110 can be an unfiltered assembly. More particularly, the configuration of the electrical feedthrough assembly 110 can include an active component, e.g., the distal electrode 104, isolated from a ground component (e.g., the flange 208) by an insulator 306. The electrical feedthrough assembly 110 for the biostimulator 100 can include the distal electrode 104, which may further include an electrode body 302 and/or an electrode tip 304. In implementations of the present disclosure, the electrode tip 304 may be mounted on the electrode body 302, e.g., on a distal end of the electrode body 302, as illustrated in FIG. 3.

The electrical feedthrough assembly 110 may have an insulator 306 surrounding a portion of the electrode body 302. More particularly, the insulator 306 can contain and separate the conductive electrode body 302 from a mounting wall 308 of the flange 208, which may also be conductive. The insulator 306 can be formed from an alumina ceramic or other insulative material. Accordingly, the insulator 306 can electrically insulate the distal electrode 104 from the flange 208. As described above, the flange 208 can include a thread 310, e.g., an external thread on an outer surface of mounting wall 308, which may form the threaded connection 210 between the electrical feedthrough assembly 110 and the helix mount 212 (as illustrated in FIG. 2). In implementations in which the electrical feedthrough assembly is bonded, press-fit, or otherwise coupled to the helix mount 212, the thread 310 may be omitted or the flange 208 may include other surface features adapted for coupling the feedthrough assembly 110 to the helix mount 212.

Figure 4:
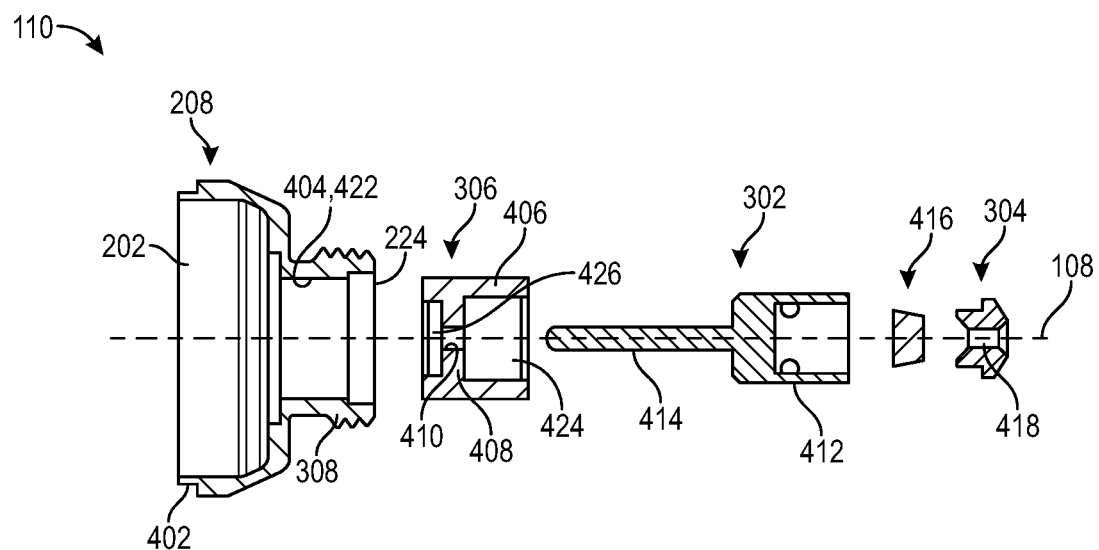
FIG. 4 is an exploded longitudinal sectional view of the electrical feedthrough assembly of FIG. 3.

FIG. 4 is an exploded view of the electrical feedthrough assembly 110. As illustrated in FIG. 4, the flange 208 can include a mounting lip 402 to engage a distal end of the housing 102 (e.g., as illustrated in FIG. 2). As illustrated in FIG. 2 and described above, a hermetic weld 209 can be formed around the mounting lip 402 to seal the electronic compartment 202 between the flange 208 and the housing 102. In one implementation, the flange 208 includes a mounting hole 404 that, when the biostimulator 100 is assembled, extends distally from the electronics compartment 202 along the longitudinal axis 108 and through a distal surface 224 of the flange 208 to a surrounding environment. More particularly, the mounting hole 404 provides a channel between the electronics compartment 202 and the surrounding environment. The mounting wall 308 of the flange 208 can extend around the mounting hole 404. For example, an inner surface 422 of the mounting wall 308 can define the mounting hole 404.

In one implementation and as further illustrated in FIG. 4, the insulator 306 has an insulator wall 406 extending distally from an insulator base 408. In one implementation, the insulator wall 406 can be cylindrical, having an outer diameter and an inner diameter; however, other insulator shapes may be used in other implementations of the present disclosure. The outer diameter of the insulator wall 406 can be sized to fit within the mounting hole 404 of the flange 208. In certain implementations, the insulator base 408 can be a lateral wall extending across the interior of the insulator 306 orthogonal to the longitudinal axis 108. More particularly, the insulator wall 406 can be a transverse wall separating a distal cavity 424 of the insulator 306 from a proximal cavity 426 of the insulator 306, with the cavities 424, 426 being radially inward from the insulator wall 406. In one implementation, an insulator hole 410 extends through the insulator base 408 along the longitudinal axis 108. Accordingly, when the insulator 306 is mounted within the mounting hole 404 of the flange 208, the insulator hole 410 provides a channel between the electronics compartment 202 and the surrounding environment.

In implementations of the present disclosure, the insulator 306 may include one or more insulator holes, each providing a feedthrough channel. The feedthrough channels can receive corresponding pins (such as pin 414, discussed below in further detail) of the electrode body 302. Accordingly, the electrical feedthrough assembly 110 can allow multi-faceted pacing or sensing feedthroughs to increase device capability. For example, the feedthrough pins can provide multi-site pacing, helix strain measurement, etc. A multi-polar feedthrough can provide activation of several components of the biostimulator 100, facilitating alternate pacing, sensing, or communication options. The increased capability may also be facilitated by providing several power and/or data feeds into the electronics compartment 202.

Feedthrough assemblies 110 in accordance with the present disclosure may include a monolithic electrode body 302. For example, the monolithic electrode body 302 can have several distinct portions that are integrally formed with each other. In one implementation, the electrode body 302 includes a cup 412 and a pin 414 that are integrally formed such that the electrode body 302 is monolithic, or, in other words, has a unitary or single-piece construction. More particularly, the cup 412 and the pin 414 can be formed from a single blank of material, as described below, to produce the electrode body 302 such that the electrode body 302 does not have any seams, welds, etc. As illustrated in FIG. 4, the pin 414 can be sized to fit through the insulator hole 410 of the insulator 306, and the cup 412 can be sized to fit within the distal cavity 424 of the insulator 306. Accordingly, the monolithic electrode body 302 provides an electrical pathway from the electronics compartment 202 proximal to the insulator base 408 to the cup 412 distal to the insulator base 408.

The cup 412 and the pin 414 can serve as the electrically active path from the electronics assembly 204 within the electronics compartment 202 (each illustrated in FIG. 2) to the patient-contacting pacing electrode tip 304. The integrally formed cup 412 and pin 414 can be of the same material. For example, and without limitation, the electrode body 302 can be formed from 90/10 platinum/iridium alloy or another suitable conductive alloy.

The biostimulator 100, and more particularly the electrical feedthrough assembly 110, can include a filler 416, such as a monolithic controlled release device (MCRD). The filler 416 is described in further detail below, however by way of introduction and without limitation, the filler 416 may include a therapeutic material, and can be loaded into the cup 412. Accordingly, the filler 416 can deliver a specified dose of a therapeutic agent, e.g., a corticosteroid, into target tissue at an implantation site of the biostimulator 100 within a patient.

The electrode tip 304 can be mounted on the electrode body 302 after the filler 416 is loaded into the cup 412. In one implementation, the electrode tip 304 includes a tip hole 418 extending through the electrode tip 304 along the longitudinal axis 108. The tip hole 418 may provide a channel between the interior of the cup 412 and the surrounding environment. Accordingly, therapeutic agent eluted by the filler 416 can pass through the tip hole 418 to the target tissue at the implantation site of the biostimulator 100. In other implementations, the electrode tip 304 and/or the electrode body 302 may include other openings or ports through which fluid may enter and exit the cup 412. The electrode tip 304 can be conductive, and electrically in contact with the electrode body 302, such that pacing impulses transmitted through the electrode body 302 from the electronics assembly 204 can travel through the electrode tip 304 to the target tissue.

In certain implementations, each of the components of the electrical feedthrough assembly 110 may be symmetrically formed about the longitudinal axis 108. For example, the cross-sectional area of the electrode body 302 illustrated in FIG. 4 can be swept about the longitudinal axis 108 such that the pin 414 and the cup 412 have cylindrical profiles. In other implementations, the profiles of the one or more of the components of the electrical feedthrough assembly 110 may be non-cylindrical. For example, a cross-section of the electrode body 302 taken about a transverse plane extending orthogonal to the longitudinal axis 108 may reveal an outer surface of the pin 414 and/or the cup 412 that is square, pentagonal, elliptical, etc., or any other suitable shape. Accordingly, the particular shapes illustrated in the figures are provided by way of example only and not necessarily by way of limitation.

Figure 5:
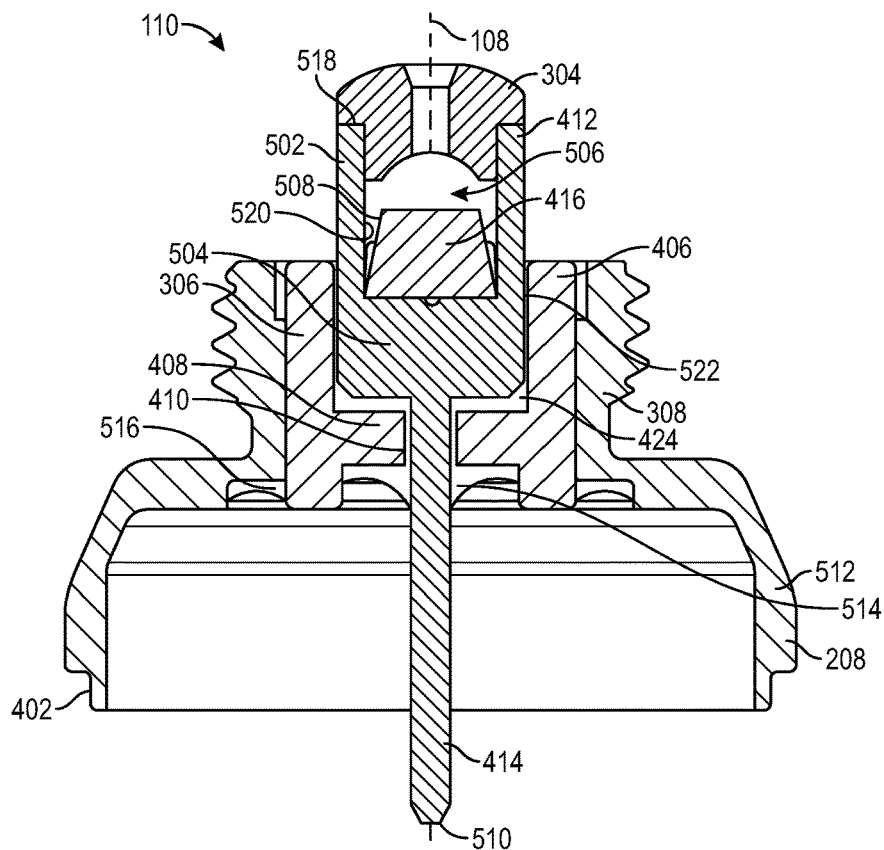
FIG. 5 is a longitudinal sectional view of the electrical feedthrough assembly of FIG. 3.

Referring now to FIG. 5, a longitudinal sectional view of the electrical feedthrough assembly 110 in the assembled state is provided. As illustrated in FIG. 5, the cup 412 can include an electrode wall 502 extending distally from an electrode base 504. In certain implementations, the electrode wall 502 can be a cylindrical wall having an outer surface facing the surrounding environment, and an inner surface facing an interior of the cup 412. The interior of the cup 412 can be an electrode cavity 506 defined between the electrode base 504 and the electrode tip 304 into which the filler 416 is loaded and within which the filler 416 for delivery to the target site. The filler 416 can have an outer surface 508 facing an inner surface 520 of the electrode wall 502. Accordingly, the inner surface 520 of the electrode wall 502 can extend around both the electrode cavity 506 and the filler 416. As described below, the electrode body 302 may include one or more retention features on the inner surface 520 of the electrode wall 502 or otherwise disposed within the electrode cavity 506 to retain the filler 416 at a predetermined location within the electrode cavity 506 without impeding agent elution.

In one implementation, the insulator wall 406 extends around the electrode wall 502 and/or the electrode base 504. For example, the electrode body 302 can have an outer surface 522 sized and shaped to fit within the distal cavity 424 of the insulator 306, and thus, an inside surface of the insulator wall 406 can face the outer surface 522 of the electrode body 302. As described above, the pin 414 of the electrode body 302 may extend proximally through the insulator hole 410. For example, the pin 414 can extend proximally from the electrode base 504 along the longitudinal axis 108 to a proximal end 510 of the electrode body 302. Accordingly, when the bio stimulator 100 is assembled, the pin 414 can extend proximally from the electrode base 504, through the insulator hole 410, and into contact with the electrical connector 206 of the electronics assembly 204 (e.g., as shown in FIG. 2). In this arrangement, the insulator base 408 is located proximal to the electrode base 504.

The flange 208 can include a shoulder 512 extending between the mounting wall 308 and the mounting lip 402. As illustrated in FIG. 2, the shoulder 512 may define a distal portion of the electronics compartment 202 when the electrical feedthrough assembly 110 is mounted on the housing 102. Accordingly, the shoulder 512 can extend around the pin 414 of the electrode body 302. Similarly, the mounting wall 308 of the flange 208 can extend around the insulator wall 406 and the insulator 306 can have an outer surface 524 sized and shaped to fit within the mounting hole 404 of the flange 208.

Based on the assembled structure described above, it can be appreciated that the individual components of the electrical feedthrough assembly 110 can be fit together during assembly, e.g., during a method of manufacturing the electrical feedthrough assembly 110. For example, in an example operation, the pin 414 can be inserted through the insulator hole 410 of the insulator 306. When the pin 414 is installed in the insulator hole 410, a proximal face of the electrode base 504 can face a distal face of the insulator base 408.

In a subsequent example operation, the electrode body 302 can be bonded to the insulator 306. The bond between the electrode body 302 and the insulator 306 can provide a mechanical attachment between the components, as well as a seal between the pin 414 and the insulator base 408 to prevent ingress or egress of fluids or energy source chemicals through portions of the insulator hole 410 that is not plugged by the pin 414. Thus, the bond between the components can be a hermetic seal. For example, the pin 414 can be bonded to the insulator 306 by a braze joint 514. The braze joint 514 can include, but is not limited to, gold brazing that flows at least partially into the insulator hole 410 to secure and seal the pin 414.

In another subsequent example operation, the insulator 306 can be inserted into the mounting hole 404 in the flange 208 such that the insulator 306 is located at a predetermined longitudinal location within the mounting hole 404. For example, the insulator 306 can be positioned such that the distal surface of the mounting wall 308 and a distal surface of the insulator wall 406 are longitudinally collocated, e.g., as illustrated in FIG. 5. Accordingly, the gasket 214 (shown in FIG. 2) may more easily seal against the distal surface of the mounting wall 308 and the distal surface of the insulator wall 406 due to the two distal surfaces 224, 526 being flush with each other. Similarly, the insulator 306 can be positioned such that a proximal surface of the mounting wall 308 and a proximal surface of the insulator wall 406 are longitudinally collocated. For example, the proximal surface of the insulator wall 406 can be longitudinally aligned with a proximally facing interior surface of the shoulder 512 of the flange 208. In certain implementations, the insulator 306 may not occupy the portion of the electronics compartment 202 that is contained by the shoulder 512, e.g., the insulator 306 may be inserted such that a proximal surface of the insulator is flush with a distal interior surface of the shoulder 512. As such, the space available within the electronics compartment 202 and/or the housing can be used for electronic circuitry and/or the energy source, rather than for the insulator 306. Accordingly, the energy source, e.g., the battery, can be lengthened and/or the housing 102 can be made smaller. A smaller overall footprint of the bio stimulator 100 can be beneficial to device implantation and device efficacy.

In still another operation, the insulator 306 can be bonded to the flange 208. The bond between the insulator 306 and the flange 208 can provide a mechanical attachment between the components, as well as a seal between the insulator wall 406 and the mounting wall 308 to prevent ingress or egress of fluids or energy source chemicals through a portion of the mounting hole 404 that is not plugged by the insulator 306. Accordingly, the bond between the components can be a hermetic seal. For example, and without limitation, the insulator 306 can be bonded to the flange 208 by a second braze joint 516. The second braze joint 516 can include gold brazing that flows at least partly into the mounting hole 404 to secure and seal the insulator 306.

Figure 6:
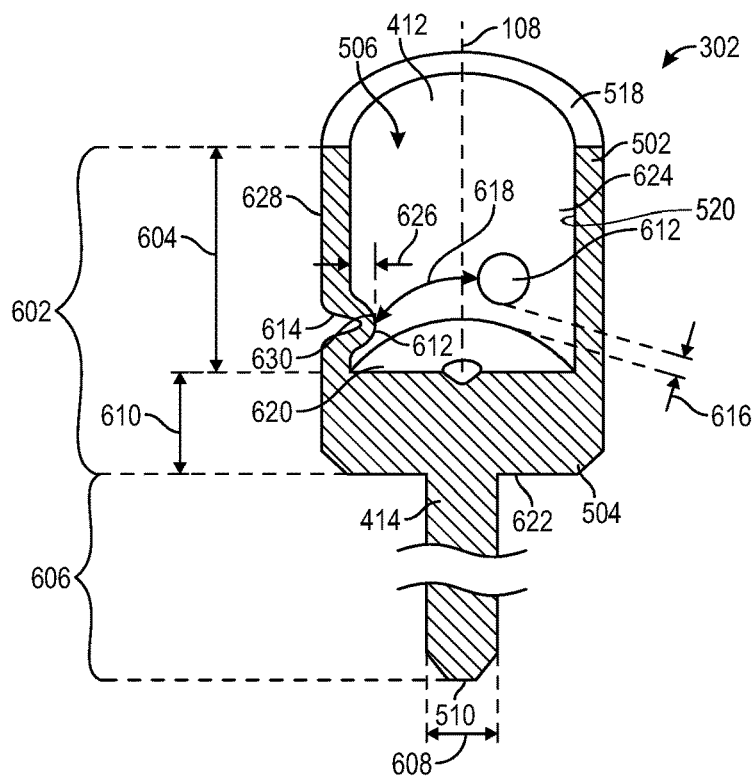
FIG. 6 is a perspective sectional view of an electrode body of the electrical feedthrough assembly of FIG. 3.
Figure 13:
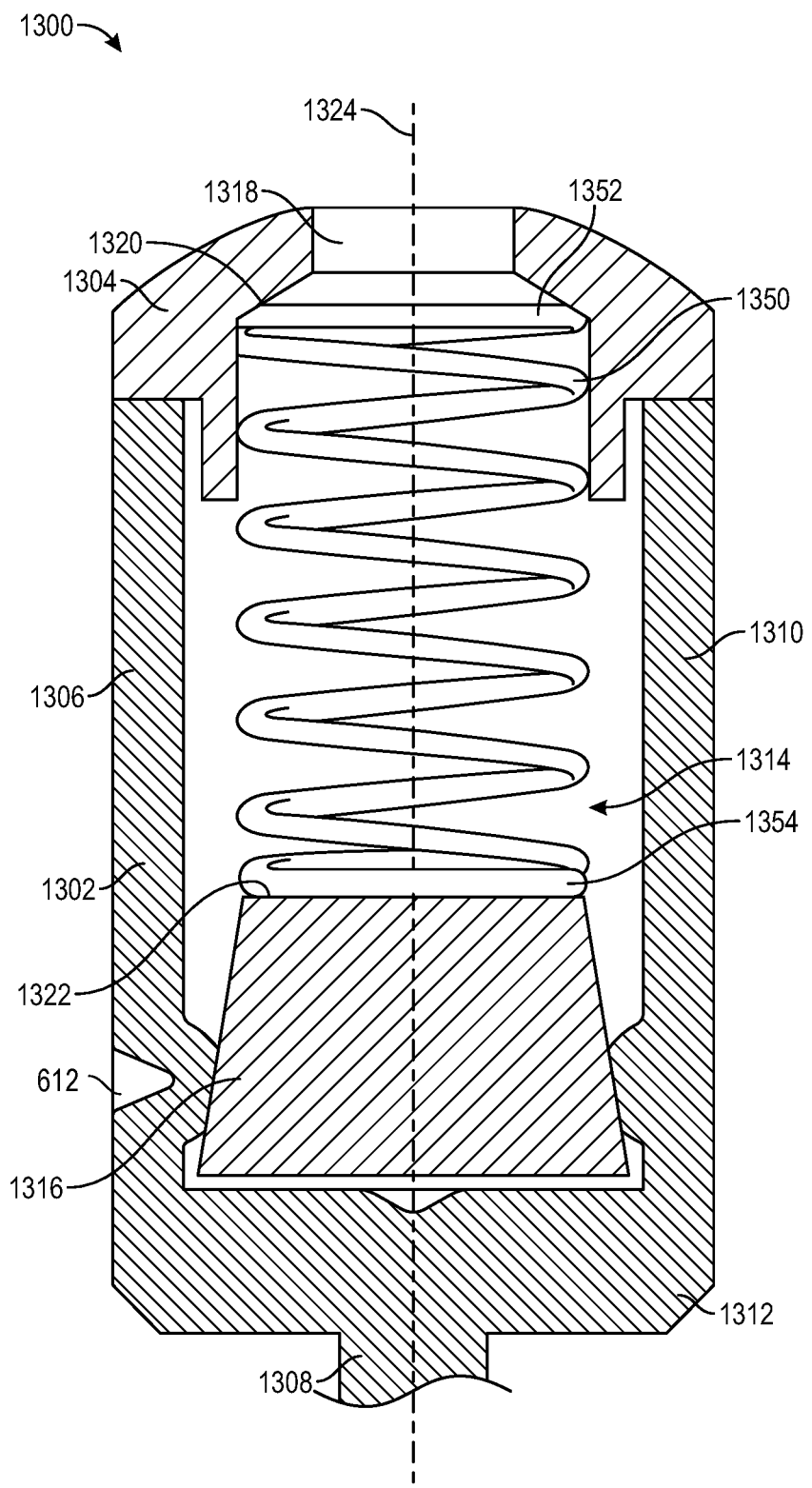
FIG. 13 is a longitudinal sectional view of an alternative electrode according to and for use with biostimulators according to the present disclosure, the electrode including a spring retaining element.
Figure 14:
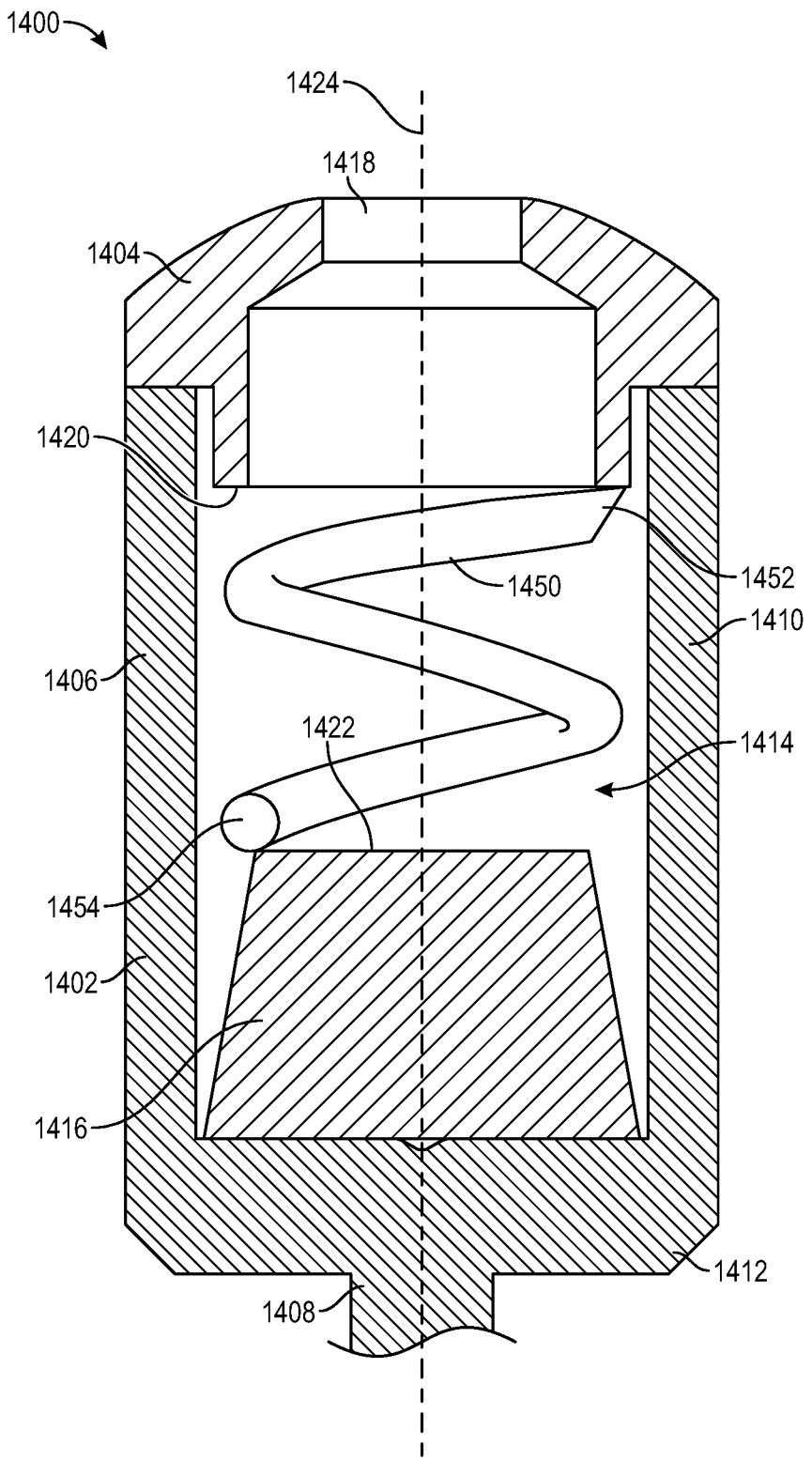
FIG. 14 is a longitudinal sectional view of another alternative electrode according to and for use with biostimulators according to the present disclosure, the electrode including a coil retaining element.
Figure 15:
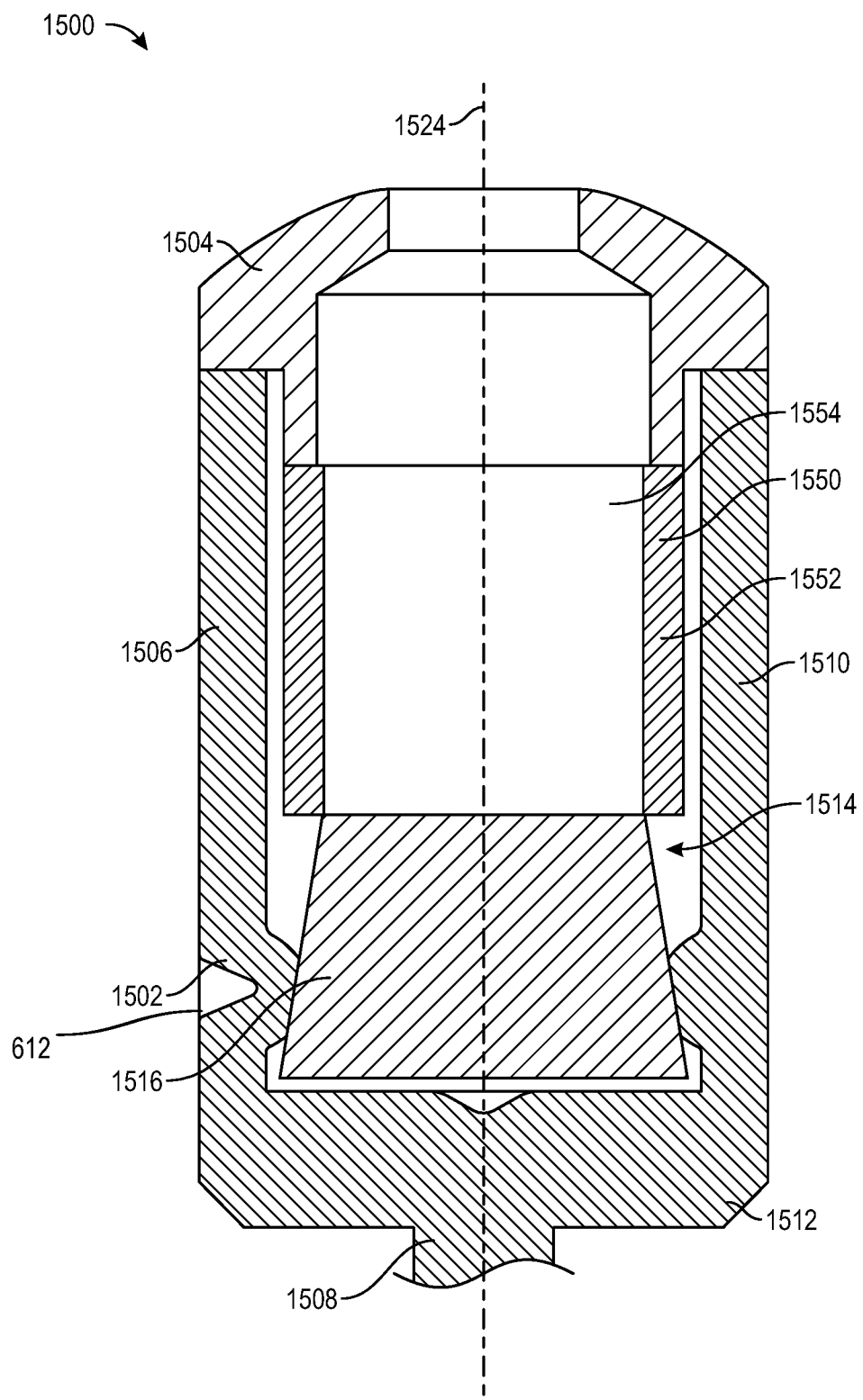
FIG. 15 is a longitudinal sectional view of yet another alternative electrode according to and for use with biostimulators according to the present disclosure, the electrode including a tubular spacer retaining element.

In yet another example operation, one or more retention features may be formed, extended, or otherwise disposed within the electrode cavity 506 to retain the filler 416. For example, as illustrated in FIG. 6 and discussed below in further detail, at least some implementations of the present disclosure may include protrusions (such as protrusions 612, shown in FIG. 6) that extend inwardly from the inner surface 520 of the electrode wall 502 and into the electrode cavity 506. The protrusions 612 can have various suitable shapes and structures, but, in general, are configured to retain the filler 416 at a predetermined location within the electrode cavity 506. Accordingly, in certain implementations of the present disclosure, the operation of forming, extending, or otherwise disposing the one or more retention features may include forming the protrusions. Non-limiting examples of techniques for forming the protrusions are described below along with their respective resulting structures. In other implementations (examples of which are illustrated in FIGS. 13-15 and described below in further detail), the one or more retention features may additionally or alternatively include a spacer or similar component inserted into the electrode cavity 506 and configured to retain the filler 416 at a predetermined location within the electrode cavity 506. For example, and without limitation, the retention feature may be a tubular spacer, a spring, or a coil disposed within the electrode cavity 506. In still other implementations, the retention feature may be in the form of legs or similar protrusions extending proximally from the electrode tip 304 into the electrode cavity 506 when the electrode tip 304 is assembled with the electrode body 302. Examples of such implementations are illustrated in FIGS. 16A-17B and discussed below in further detail.

In another example operation, the filler 416 can be inserted in the electrode cavity 506. In certain implementations, insertion of the filler 416 may occur after the retention feature is formed, extended, or otherwise disposed within the electrode cavity 506. For example, in implementations including retention features in the form of inwardly extending protrusions, the filler 416 is loaded into the electrode cavity 506 subsequent to formation of the protrusions, e.g., by pushing the filler 416 past the protrusions. By doing so, the protrusions may be placed in contact with the outer surface 508 of the filler 416, thereby retaining the filler 416 at a predetermined location within the electrode cavity 506. Alternatively, the filler 416 may be inserted into the electrode cavity 506 first and the protrusions may be formed subsequently, e.g., by crimping or indenting the electrode wall 502 defining the electrode cavity. Similarly, in implementations in which the retention feature is an item disposed within the electrode cavity 506 (e.g., a spring, coil, or tubular spacer), the filler 416 may be inserted into the electrode cavity 506 first followed by the retention feature such that the retention feature is positioned distally within the electrode cavity 506 relative to the filler 416.

In still another example operation, the electrode tip 304 is mounted on a distal end 518 of the electrode body 302. For example, the electrode tip 304 can be placed in contact with the distal end 518 around a circumference of the distal end 518. The electrode tip 304 is then joined to the electrode body 302 by a circumferential bond. For example, an adhesive or thermal weld may be formed between the distal end of the cup 412 and the electrode tip 304.

In implementations including retention features in the form of legs or protrusions extending distally from the electrode tip 304 (e.g., as illustrated in FIGS. 16A-17B and discussed below in further detail), the foregoing operations of inserting the retention feature and mounting the electrode tip 304 may generally be combined. For example, during assembly, the filler 416 may be inserted into the electrode cavity 506. Subsequently, the electrode tip 304 may be positioned on the distal end 518 of the electrode body 302 such that the protrusions of the electrode tip 304 extend into the electrode cavity 506 in order to retain the filler 416. Once mounted, the electrode tip 304 may then be joined to the electrode body 302, e.g., by welding, adhesive, or other similar joining method.

Referring to FIG. 6, a perspective sectional view of an electrode body 302 is shown in accordance with an implementation of the present disclosure. In addition to the assembly operations described above, the components of the electrical feedthrough assembly 110 may be manufactured using processes that contribute to device performance. For example, the electrode body 302 can be formed monolithically from a material blank. By way of example, the material blank can be a cylindrical plug having an outer diameter equal to or greater than a transverse dimension of the cup 412, and a length equal to or greater than the length between the distal end 518 and the proximal end 510 of the electrode body 302. The material blank can be shaped using mechanical machining, electrical discharge machining, laser cutting, grinding, or other processes to remove material and otherwise shape the blank into the form of the electrode body 302. Accordingly, the electrode body 302 can have continuous and consistent material properties throughout the body mass, as compared to, e.g., bonding a pin component to a separately formed cup component.

It will be appreciated that monolithically forming the electrode body 302 is not only less complex and less expensive than joining several components, but also, the monolithically formed electrode body 302 may perform more effectively than the multi-component electrode body. More particularly, joints between separate pin and cup components may not conduct pacing impulses uniformly and/or fluids or battery chemistries can attack and pass through such joints, leading to ineffective pacing or device failure. By contrast, the monolithically formed electrode body 302 does not have a weld chemistry, burnishing, etc., which can leave contaminants on the electrode surface. Furthermore, any particulate remaining on the electrode surface from the manufacturing operation can be fully and easily cleaned, e.g., using an ultrasonic bath, with a reduced likelihood that the particles will remain lodged in a crevice or seam of the electrode body 302. Accordingly, the monolithically formed electrode body 302 provides several benefits as compared to multi-component electrodes.

In one example operation and with reference to the electrode body 302 of FIG. 6, the cup 412 of the electrode body 302 is formed in a distal portion of the electrode blank, e.g., the cup 412 is formed from a distal portion 602 of the electrode body 302. In one implementation of the present disclosure, forming the cup 412 includes removing material from the distal portion 602 to form the electrode cavity 506 within the electrode wall 502. Removal of the material can include, but is not limited to, drilling into the material blank. The drilling operation can extend from the distal end 518 of the electrode wall 502 to a distal face 620 of the electrode base 504, and thus, the electrode cavity 506 can have a cavity height 604. By way of non-limiting example, in at least some implementations of the present disclosure, the cavity height 604 can be from and including about 0.050 inches to and including about 0.1 inches, e.g., 0.060 or 0.079 inches. Accordingly, electrode wall 502 extends distally from the electrode base 504 around the electrode cavity 506 located on the longitudinal axis 108.

In another example operation, the pin 414 of the electrode body 302 is formed in a proximal portion of the electrode blank, e.g., pin 414 is formed from a proximal portion 606 of the electrode body 302. In one implementation, forming the pin 414 includes removing material from the outer surface of the proximal portion 606 to form the pin 414. Removal of the material can include, without limitation, turning the material blank down in a lathe, or grinding the outer surface to form the pin 414 such that the pin 414 has a pin diameter 608. The machining processes can form the pin 414 integrally with the cup 412. Accordingly, the pin 414, which is integral to the cup 412, can extend proximally from the electrode base 504 along the longitudinal axis 108 to the proximal end 510.

Removal of material to form the cup 412 and removal of material to form the pin 414 can be performed in different operations. The operations can define a location of a proximal face 622 and the distal face 620 of the electrode base 504, and thus, can control a base thickness 610 of the electrode base 504. By way of non-limiting example, the base thickness 610 can be from and including about 0.010 inches to and including about 0.05 inches, e.g., 0.015 or 0.034 inches.

In certain implementations of the present disclosure, one or more protrusions 612 are located on an inner surface 624 of the electrode wall 502. The protrusions 612 of the electrode wall 502 can extend inwardly into contact with the outer surface of the filler (not shown). For example, each protrusion 612 can extend radially from the inner surface 624 to a tip or end of the protrusion 612 between the electrode wall 502 and the longitudinal axis 108. In one example implementation, the protrusions 612 can be integrally formed with the electrode wall 502. For example, each protrusion 612 can be a dimple formed by coining or indenting an outer surface 628 of the electrode wall 502.

In another example, the cup is machined as a solid component. Each protrusion 612 is then formed by indenting a dimple on the electrode wall 502 by punching into the electrode wall 502 from the outer surface 628 of the electrode wall 502. By forming an indentation 614 in the outer surface 628 of the electrode wall 502, the inner surface 620 of the electrode wall 502 can deform to a protrusion height 626 radially inward from the inner surface 624 of the rest of the cup 412. Thus, the protrusions 612 can penetrate into the cup 412 to serve as a retention feature for the filler.

Each protrusion 612 can have respective dimensions. For example, the protrusions 612 can have the protrusion height 626 measured between an apex 630 of the protrusion and the inner surface 624 of the electrode wall 502 around the protrusion 612. Furthermore, the indentation of the electrode wall 502 can be located at a location on the outer surface 628 of electrode wall 502 such that a protrusion offset 616 measured between the distal face 620 of the electrode base 504 and the apex 630 of the protrusion 612 is a predetermined distance. By way of example, the protrusion offset 616 can be from and including about 0.010 inches to and including about 0.050 inches, e.g., 0.012 inch.

In certain implementations of the present disclosure, several protrusions 612 may be spaced along the inner surface 520 of electrode wall 502. By way of example, electrode body 302 can have two or more protrusions 612 separated from each other by a separation angle 618. The several protrusions 612 can be spaced equidistantly about the longitudinal axis 108. For example, when the electrode body 302 has two protrusions 612, the protrusions 612 can be separated about longitudinal axis 108, the separation angle 618 may be equal to about 180 degrees. Similarly, when the electrode body 302 has three protrusions 612, the separation angle 618 between each protrusion 612 may be equal to about 120 degrees. Alternatively, the separation angle 618 between pairs of adjacent protrusions may vary such that the protrusions 612 are not distributed evenly about the longitudinal axis 108. In certain implementations, each protrusion 612 may have a same protrusion offset 616 such that all protrusions are distributed along a transverse plane orthogonal to the longitudinal axis 108. Alternatively, the protrusions 612 may have different protrusion offsets 616, e.g., at least one of the protrusions 612 can be at a different longitudinal location than another protrusion 612.

Figure 7:
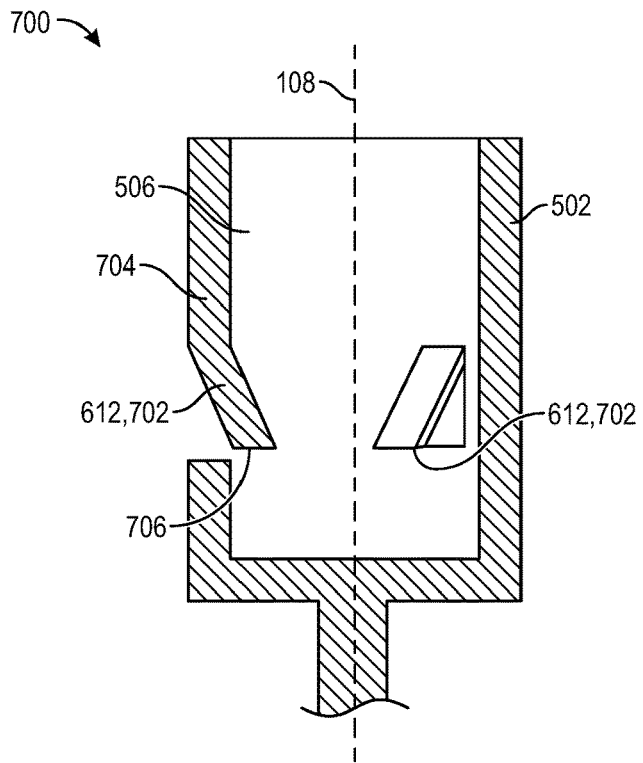
FIGS. 7 and 8 are longitudinal sectional views of alternative electrode bodies that may be used in electrical feedthrough assemblies in accordance with the present disclosure, the electrode bodies having various internal protrusions to retain a filler.

Referring to FIG. 7, a longitudinal sectional view of an alternative implementation of an electrode body 700 in accordance with the present disclosure is provided that includes various protrusions 612 to retain a filler (e.g., filler 416 of FIGS. 4 and 5) within an electrode cavity 506 defined within the electrode body 700. As illustrated in FIG. 7, in certain implementations, the protrusions 612 can be tabs 702 that are bent inward from the electrode wall 502 toward a longitudinal axis 108 of the electrode body 700. For example, the electrode wall 502 can have a laser cut trench or slot that extends around the tab 702. The tab 702 can then be pressed inward to bend about a tab base 704. More particularly, the tab 702 can extend from the tab base 704 to a tab tip 706. When the tab 702 is bent inward, the tab tip 706 can be radially inward of the electrode wall 502, and thus, may be placed in contact with the filler to retain the filler within the electrode cavity 506.

Figure 8:
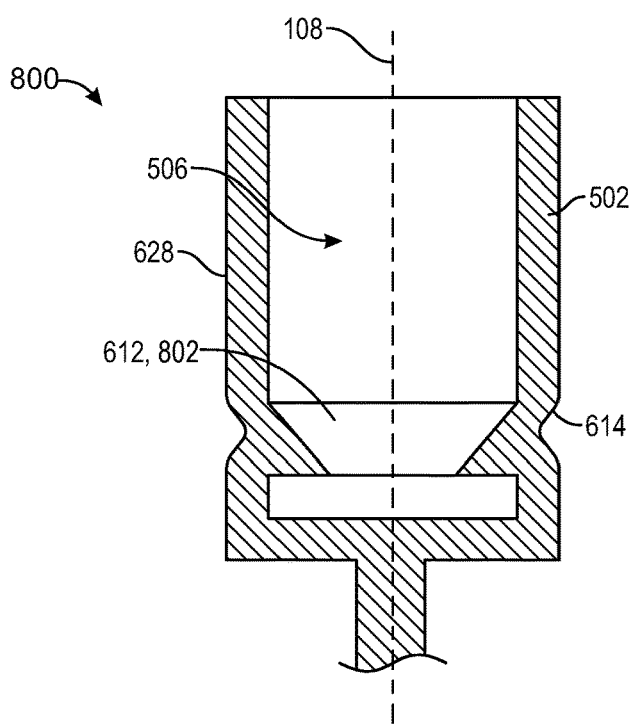

Referring to FIG. 8, a longitudinal sectional view of another alternative implementation of an electrode body 800 in accordance with the present disclosure is provided. The electrode body 800 similarly includes a protrusion 612, 802 to retain a filler within an electrode cavity 506 defined by the electrode body 800, the protrusion 612, 802 extending circumferentially about a longitudinal axis 108 of the electrode body 800. For example, the electrode wall 502 can be swaged along an outer surface 628 of the electrode wall 502 to form an indentation 614 extending about the outer surface 628. In other words, the electrode wall 502 can be deformed radially inward to such that the protrusion 612 is formed as a circumferential lip 802 around the electrode cavity 506. The circumferential lip 802 can be radially inward of the electrode wall 502, and thus, may be placed in contact with filler. It will be appreciated that the protrusion 612 whether coined, bent, or swaged, can share the geometric features described above with respect to FIG. 6, e.g., protrusion height, protrusion offset, or separation angle.

Figure 9:
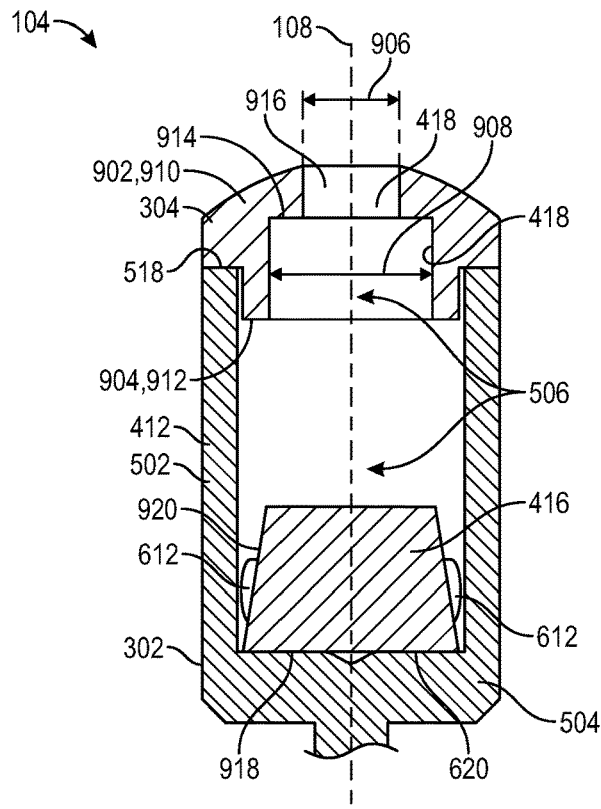
FIGS. 9-11 are longitudinal sectional views of a filler disposed within various electrodes in accordance with the present disclosure, each of the electrodes having respective elution port configurations.

Referring to FIG. 9, a longitudinal sectional view of the electrode 104 of FIGS. 1-6 is provided. As illustrated, the electrode 104 defines an electrode cavity 506 within which a filler 416 is disposed. The electrode 104 further includes an electrode tip 304 forming a distal tip end 902 facing the surrounding environment and opposite a proximal tip end 904. The distal tip end 902 and the proximal tip end 904 can be on respective faces 910, 912 of the electrode tip 304, and the faces 910, 912 can have respective shapes. For example, the distal face 910 can be curved or conical, and the proximal face 912 can be flat. In one implementation, the distal face 910 of the electrode tip 304 is covered by a coating (not shown) that increases a virtual surface area of the electrode tip 304 and controls current density. For example, the coating can be a titanium nitride coating. As described above, the electrode tip 304 may define a tip hole 418 extending through the electrode tip 304 along the longitudinal axis 108 from the distal tip end 902 to the proximal tip end 904. The tip hole 418 can be a through hole, and thus, can have a first diameter 906 at the distal tip end 902 and a second diameter 908 at the proximal tip end 904 of the tip electrode 304.

In one implementation, the first diameter 906 of the tip hole 418 can be less than the second diameter 908 of the tip hole 418. For example, as illustrated in FIG. 9, the tip hole 418 can include a counterbore 914 extending from the proximal tip end 904 to an intermediate location between the distal tip end 902 and the proximal tip end 904. Furthermore, the tip hole 418 can include a through hole 916 extending from the distal tip end 902 to the counterbore 914, with the through hole 916 being narrower than the counterbore 914. Accordingly, the portion of the tip hole 418 corresponding to the counterbore 914 can increase a volume of the electrode cavity 506 to accommodate expansion of the filler 416 or movement/compression of a retention element when the biostimulator is implanted at the target site. More particularly, the portion of the tip hole 418 corresponding to the counterbore 914 can form a distal portion of the electrode cavity 506. Although the first diameter 906 may vary in size, the first diameter 906 is generally sized to cover and retain the filler 416 within the electrode cavity 506.

During use, the filler 416 can be located in the electrode cavity 506 at a predetermined position. For example, in implementations of the present disclosure including retention features in the form of protrusions 612, the filler 416 can be disposed within the electrode cavity 506 radially between the protrusions 612 such that the protrusions 612 grip an outer surface 920 of the filler 416. In at least certain implementations, when the filler 416 is located between the protrusions 612, a proximal face 918 of the filler 416 can be adjacent to a distal face 620 of the electrode base 504.

The filler 416 may include a therapeutic agent contained within a carrier matrix. For example, the carrier matrix can be a silicone matrix, e.g., a monolithic silicone plug, which is impregnated with the therapeutic agent. The therapeutic agent can in turn be contained within pores of the silicone matrix. In such implementations, the filler 416 may also be referred to as a monolithic controlled release device (MCRD). In at least one implementation, the therapeutic agent can include a corticosteroid, such as dexamethasone sodium phosphate, dexamethasone acetate, etc.

When the bio stimulator is implanted at the target site, blood can flow into the electrode cavity 506 through the tip hole 418 and cause the filler 416 to elute the therapeutic agent. Elution of the filler 416 can be controlled by its own geometry, as well as by a size of the electrode cavity 506 and the geometry of the electrode body 302. For example, the protrusions 612 can grip the filler 416 along the outer surface 920 without covering the entire outer surface 920. As a result, the uncovered portions of the outer surface 920 remain unblocked by the electrode body 302 and, therefore, able to be exposed to blood entering the electrode cavity 506. The filler 416 can be retained primarily by the protrusions 612 in the cup 412 of the electrode body 302 to allow the exposed surface area of the outer surface 920 to be maximized for elution consistency. More particularly, the protrusions 612 can keep the filler 416 from dislodging while still allowing the outer surface 920 of the filler 416 to be exposed. Accordingly, the therapeutic agent can flow, or weep, from the uncovered portion of the outer surface 920 through the tip hole 418 to the target tissue. When the therapeutic agent is consistently released into the target tissue, the controlled dose can reduce inflammation associated with the device implantation.

Figure 10:
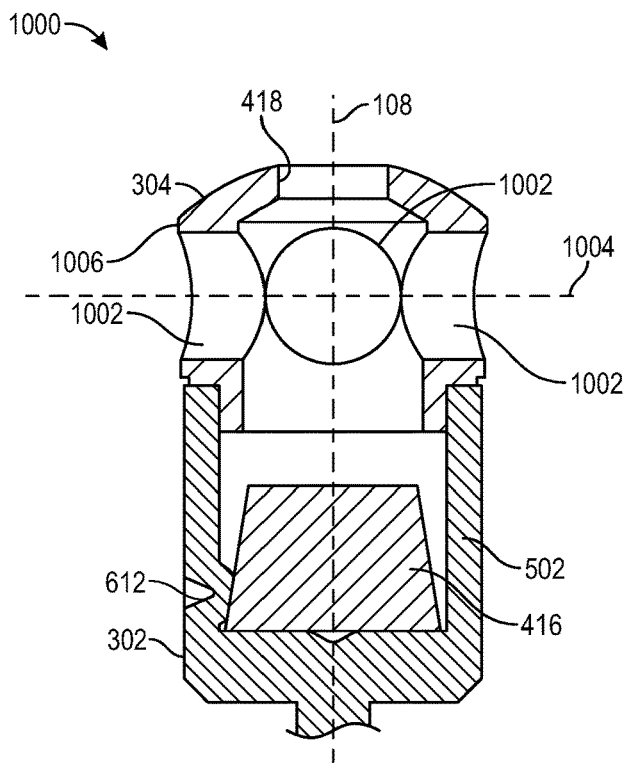

FIG. 10 is a longitudinal sectional view of an alternative electrode 1000 in accordance with the present disclosure. As illustrated, the electrode 1000 includes a proximal end of electrode body 302 and electrode tip 304 that together define an electrode cavity 506 within which a filler 416 is disposed. The filler 416 is illustrated as being retained within the electrode cavity 506 by one or more protrusions 612 extending inwardly from an electrode wall 502 of the electrode body 302. In contrast to previously illustrated implementations, the electrode 1000 further defines weeping holes 1002 in the electrode tip 304. The electrode 1000 can include one or more weeping holes 1002 instead of, or in addition to, a tip hole 418. More particularly, the weeping holes 1002 can extend through one or more of the electrode body 302, e.g., an electrode wall 502 of the electrode body 302, or the electrode tip 304. In one example implementation, the one or more weeping holes 1002 extend through a side surface 1006 of the electrode tip 304. For example, the one or more weeping holes 1002 can extend along a transverse axis 1004 that is orthogonal to the longitudinal axis 108. The transverse axis 1004 can intersect the longitudinal axis 108 along which a counterbore of the electrode tip 304 and/or a through hole of the tip hole 418 extend, and thus, the one or more weeping holes 1002 can intersect the tip hole 418. Accordingly, when the therapeutic agent elutes from the filler 416, the agent can pass through the tip hole 418 and/or the one or more weeping holes 1002 to be delivered to the target tissue.

Figure 11:
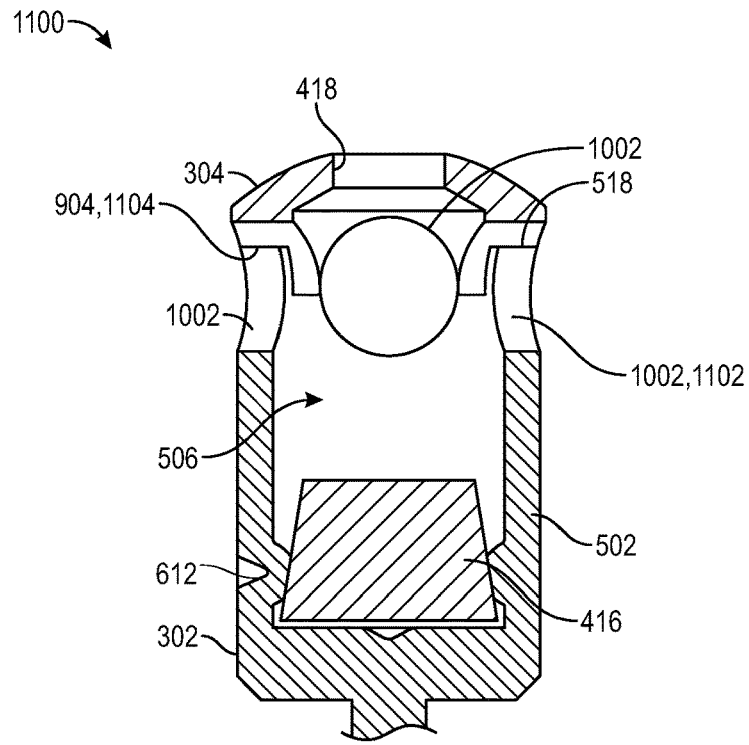

FIG. 11 is a longitudinal sectional view of a yet another electrode 1100 in accordance with the present disclosure. Similar to the previously discussed electrodes 900, 1000, the electrode 1100 includes an electrode body 302 and an electrode tip 304 that collectively define an electrode cavity 506 within which a filler 416 is disposed. The filler 416 is illustrated as being retained by one or more protrusions 612 extending inwardly from an electrode wall 502 of the electrode body 302. The electrode 1100 further defines one or more weeping holes 1002 through which blood may enter and exit the electrode cavity 506 to interact with the filler 416. As illustrated, the one or more weeping holes 1002 can extend through the electrode body 302, e.g., through the electrode wall 502. In one example implementation, the weeping holes 1002 extend through the electrode wall 502 at a distal end 518 of the electrode body 302 to form a notch 1102 in the distal end 518. The notch 1102 in the electrode wall 502 can mate with a corresponding notch 1104 at a proximal tip end 904 of the electrode tip 304 to form the weeping holes 1102. More particularly, the weeping holes 1102 can extend through one or more of the electrode wall 502 or the electrode tip 304 to intersect the electrode cavity 506. Accordingly, when the therapeutic agent elutes from the filler 416, the agent can pass through the tip hole 418 and/or the weeping holes 1002 to be delivered to the target tissue.

Figure 12:
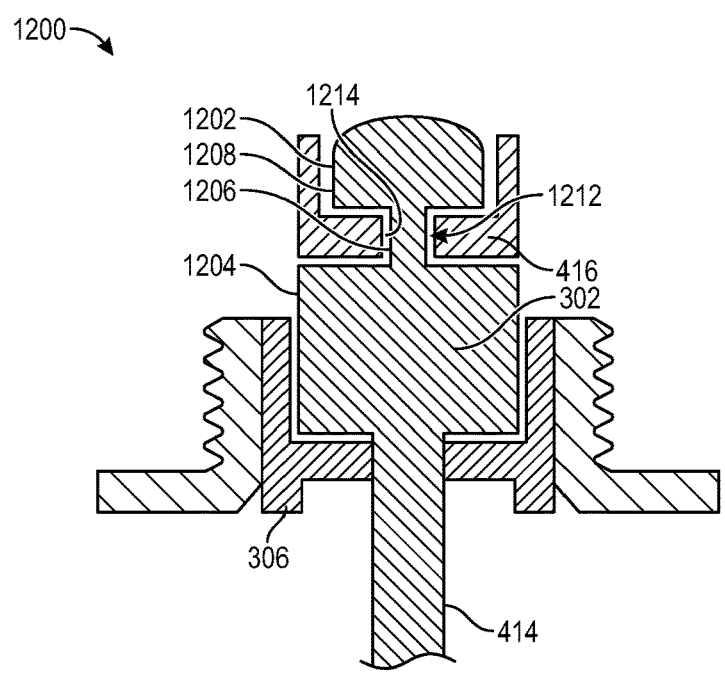
FIG. 12 is a longitudinal sectional view of another electrical feedthrough assembly according to the present disclosure, the electrical feedthrough assembly including a filler retained on an external surface of an electrode body of the electrical feedthrough assembly.

FIG. 12 is a longitudinal sectional view of an electrode assembly 1200 in accordance with the present disclosure. In contrast to FIGS. 10 and 11, the electrode assembly 1200 of FIG. 12 includes a filler 416 retained on an external surface 1208 of an electrode body 302. In such implementations, the electrode body 302 may be solid. The electrode body 302 can include a pin 414 that extends proximally through an insulator hole 410 as described above. The electrode body 302, however, may not include a cup 412 as illustrated, e.g., in FIG. 4. Accordingly, in implementations including a solid electrode body 302, there may be no electrode cavity defined within the electrode body 302, and thus, the filler 416 may instead be retained on the outer surface 1208 of the electrode body 302 rather than within an internal electrode cavity.

In one implementation, the electrode body 302 includes a body tip 1202 connected to a body core 1204 by a body neck 1206. The body neck 1206 can have an outer diameter that is smaller than that of the body tip 1202 and/or the body core 1204. The filler 416 may have a geometry that fits around one or more of the electrode body portions to be retained on the electrode body 302. For example, the filler 416 can fit within a gap 1212 between the body tip 1202 and the body core 1204. Accordingly, the filler 416 can include a through hole 1214 having a diameter that is larger than that of the body neck 1206 and/or smaller than body tip 1202. In one example implementation, the filler 416 can be resiliently stretched over the body tip 1202 such that the portion of the filler 416 located between the body tip 1202 and the body core 1204 retains the filler 416 on the electrode body 302. When the biostimulator is implanted at the target site, the therapeutic agent can elute from the filler 416 directly into the tissue rather than through an elution port.

As previously discussed in the context of FIGS. 6-8, biostimulators in accordance with the present disclosure may include electrodes having electrode bodies that define an inner electrode cavity. In certain implementations, a filler, such as a monolithic controlled release device (MCRD), may be disposed within the cavity, e.g., to provide controlled release of a therapeutic agent at an implantation site of the biostimulator. Certain electrodes in accordance with this disclosure may include a retention feature configured to retain the filler at a predetermined location within the electrode cavity. Although the particular location of the filler within the electrode cavity may vary, in general, the predetermined location within the electrode cavity is such that the filler is offset from the distal tip end. Offsetting the filler results in several advantages. For example, offsetting the filler facilitates exchange of bodily fluid within the electrode cavity, e.g., by preventing the filler from blocking a tip hole or weeping holes of the electrode such that fluid may readily flow into and out of the electrode cavity. Offsetting the filler may further ensure that a sufficient portion of the outer surface of the filler remains exposed for proper elution.

In previously discussed implementations, the retention features were generally in the form of integrally formed protrusions or tabs extending inwardly into the electrode cavity from an inner wall of the electrode body. The protrusions were positioned and distributed within the electrode cavity such that the protrusions abutted an outer surface of the filler when the filler was disposed within the electrode cavity, thereby retaining the filler. In contrast to such protrusions, other implementations of the present disclosure may include retention features in the form of insertable retention elements that may be inserted into the electrode cavity subsequent to insertion of the filler. Similar to the previously discussed protrusions, the insertable retention elements are generally configured to retain the filler at a predetermined location within the electrode cavity, thereby preventing the filler from obstructing fluid exchange within the electrode cavity and ensuring proper exposure of the filler for elution, among other things. In certain implementations, the insertable retention elements proximally bias the filler toward the electrode base. Such insertable retention elements may be used instead of or in combination with the various integrally formed retention features discussed above.

In certain implementations, the one or more retention elements advantageously add free space to the interior of the feedthrough assembly to accommodate expansion of the filler. For example, the one or more retention elements may increase the free space of the electrode cavity (by minimizing the amount of volume used by the one or more retention elements), thereby improving fluid exchange and increasing space within the electrode cavity for the filler to flow into.

FIG. 13 is a longitudinal sectional view of an example electrode 1300 according to the present disclosure including a first example retention element in the form of a spring 1350. The electrode 1300 may be implemented, for example, in the feedthrough assembly 110 of the biostimulator 100 of FIG. 1. The electrode 1300 includes an electrode body 1302 and an electrode tip 1304 coupled to the electrode body 1302. The electrode body 1302 may further include a cup 1306 and a pin 1308 that are integrally formed, such that the electrode body 1302 is monolithic. The cup 1306 can include an electrode wall 1310 extending distally from an electrode base 1312 such that the cup 1306 defines an electrode cavity 1314. A filler 1316, such as a monolithic controlled release device (MCRD) containing a therapeutic agent, may be disposed within the electrode cavity 1314. Subsequent to implantation of a biostimulator including the electrode 1300, fluid may enter the electrode cavity 1314 through a tip hole 1318 defined by the electrode tip 1304 (and/or weeping holes as illustrated in, e.g., FIGS. 10 and 11) such that the fluid may interact with the filler 1316 to elute the therapeutic agent of the filler 1316, thereby delivering the therapeutic agent to the implantation site.

As previously discussed, the filler 1316 may be retained at a predetermined location within the electrode cavity 1314 such that, among other things, the filler 1316 is prevented from migrating within the electrode cavity 1314 to obstruct the tip hole 1318 (or weeping holes, as illustrated in, e.g., FIGS. 10 and 11), to ensure that the outer surface 1322 of the filler 1316 remains sufficiently exposed for proper elution, and/or for other similar purposes. To achieve this retention, the electrode 1300 includes a spring 1350 disposed within the electrode cavity 1314 and extending along a longitudinal axis 1324 of the electrode 1300. The spring 1350 generally extends between an internal proximal surface 1320 of the electrode tip 1304 and a distal face 1322 of the filler 1316. Notably, the spring 1350 biases the filler 1316 in a proximal direction and may provide increased proximal biasing as it is compressed in response to the filler 1316 expanding within the electrode cavity 1304 as the filler 1316 reacts to bodily fluid. In at least some implementations, as the filler 1316 expands in response to contact with bodily fluid, the filler 1316 may expand into the internal volume defined by the spring 1350 and/or into interstices of adjacent turns of the spring 1350.

In certain implementations of the present disclosure, the spring 1350 is a closed end helical spring. For example, as illustrated in FIG. 13, the spring 1350 includes opposite closed ends 1352, 1354. In certain implementations, the use of a closed-ended spring may have certain advantages over other retention features. For example, and without limitation, the closed end 1352 of the closed-ended spring may generally provide relatively high contact area and flush contact with corresponding surfaces within the electrode cavity 1314 (e.g., proximal faces of the electrode tip 1304). As shown in FIG. 13, the closed end 1354 may also be configured to have relatively high and substantially flush contact with the filler 1316, thereby resulting in relatively even distribution of forces exerted on the filler 1316 by the spring 1350. Notably, the open structure of the spring 1350 still permits the filler 1316 to expand into the spring 1350 as the filler 1316 is exposed to fluid. More generally, however, the spring 1350 is designed to fit and be retained within the electrode cavity 1314 and to interact with the various surfaces of the electrode cavity 1314 such that the spring 1350 is sufficiently supported to bias or otherwise maintain the filler 1316 within a predetermined location within the electrode cavity 1314 throughout expansion of the filler 1316.

Although the dimensions and characteristics of the spring 1350 may vary based on, among other things, the dimensions of the electrode cavity 1314 and the filler 1316, in at least certain implementations the spring 1350 may have a length from and including about 0.05 inches to and including about 0.075 inches, e.g., 0.063 inches, and a diameter from and including about 0.025 inches to and including about 0.050 inches, e.g., 0.036 inches. The spring 1350 may also have a pitch from and including about 0.005 inches to and including about 0.020 inches, e.g., 0.010 inches. More generally, the spring 1350 has a length sufficient to maintain the filler 1316 at a minimum offset relative to the electrode tip 1304 and a diameter such that the filler 1316 cannot pass through spring 1350. The spring 1350 may be formed from various wires; however, in at least certain implementations, the spring 1350 is formed from a wire having a diameter from and including about 0.0020 inches to and including about 0.0040 inches, e.g., 0.0030 inches. The spring 1350 is also preferably formed from a biocompatible material, such as MP35N steel, or otherwise coated/treated to be biocompatible. In certain implementations, the material and geometry of the spring 1350 is such that the spring 1350 provides a sufficient load to the filler 1316 in order to keep the filler 1316 seated proximal in the cup 1306, but a light enough load to allows the filler 1316 to expand in a controlled manner as fluid enters the matrix. In certain implementations, the geometry and resilience of the spring 1350 configure the spring 1350 to compress without fracture.

In certain implementations, the filler 1316 can be retained by only the spring 1350 that allows the exposed surface area of the filler 1316 to be maximized for elution consistency.

In certain implementations, the filler 1316 can be retained by a combination of protrusions 612 in the cup 1306 of the electrode body 1302 and the spring 1350 that allows the exposed surface area of the filler 1316 to be maximized for elution consistency.

When the therapeutic agent is consistently released into the target tissue, the controlled dose can reduce inflammation associated with the device implantation.

In certain implementations, the distal face 1322 of the filler 1316 matches or is slightly larger in diameter than an outer diameter of the spring 1350. The filler 1316 may taper to a large enough diameter such that it would be naturally centered within the cup 1306 and engage all of the protrusions 612 in the cup 1306. In certain implementations, the volume of the filler 1316 within the cup 1306 is sufficiently small so as to provide a sufficient free volume within the electrode cavity 1314 that allows free exchange of fluids and swelling of the filler 1316 during use. As the filler 1316 expands, it may also expand into the internal volume defined by the spring 1350 and/or interstices between adjacent turns of the spring 1350.

FIG. 14 is a longitudinal sectional view of an example electrode 1400 according to the present disclosure including a second example retention element in the form of a coil 1450, which may be implemented, for example, in the feedthrough assembly 110 of the bio stimulator 100 of FIG. 1. More specifically, the electrode 1400 includes an electrode body 1402 and an electrode tip 1404 coupled to the electrode body 1402. The electrode body 1402 may further include a cup 1406 and a pin 1408 that are integrally formed such that the electrode body 1402 is monolithic. The cup 1406 can include an electrode wall 1410 extending distally from an electrode base 1412 such that the cup 1406 defines an electrode cavity 1414 within which a filler 1416 may be disposed.

The coil 1450 retains the filler 1416 at a predetermined location within the electrode cavity 1414 such that, among other things, the filler 1416 is prevented from migrating within the electrode cavity 1414 to obstruct a tip hole 1418 (or weeping holes, as illustrated in, e.g., FIGS. 10 and 11), to ensure that the outer surface of the filler 1416 remains sufficiently exposed for proper elution, and/or for other similar purposes. As illustrated, the coil 1450 is disposed within the electrode cavity 1414 such that it extends along a longitudinal axis 1424 of the electrode 1400. For example, the coil 1450 may generally extend between an internal proximal surface 1420 of the electrode tip 1404 and a distal face 1422 of the filler 1416. Similar to the spring 1350 discussed above, the coil 1450 biases the filler 1416 in a proximal direction and provides increased proximal biasing as the filler 1416 expands within the electrode cavity 1414 as the coil 1450 is compressed. As the filler 1416 expands, it may also expand into the internal volume defined by the coil 1450 and/or interstices between adjacent turns of the coil 1450.

The coil 1450 may be an open-ended coil. For example, as illustrated in FIG. 14, the coil 1450 includes opposite tips ends 1452, 1454. In certain implementations, the use of an open-ended coil may have certain advantages over other retention features. For example, and without limitation, the open-ended coil may generally occupy less volume of the electrode cavity 1414 than other retention features. In certain implementations, the tip end 1454 may also be configured to impinge upon or otherwise interfere with the filler 1416 as the filler 1416 expands, thereby improving retention of the filler 1416 within the electrode cavity 1414. More generally, however, the coil 1450 is designed to fit and be retained within the electrode cavity 1414 and to interact with the various surfaces of the electrode cavity 1414 such that the coil 1450 is sufficiently supported to bias or otherwise maintain the filler 1416 within a predetermined location within the electrode cavity 1414 even as the filler 1416 expands.

Although the dimensions and characteristics of the coil 1450 may vary, in at least certain implementations, the coil 1450 may have a length from and including about 0.020 inches to and including about 0.040 inches, e.g., 0.030 inches, and a diameter from and including about 0.020 inches to and including about 0.050 inches, e.g., 0.035 inches. The coil 1450 may also have a pitch from and including about 0.020 inches to and including about 0.040 inches, e.g., 0.030 inches. More generally, the coil 1450 has a length sufficient to maintain the filler 1416 at a minimum offset relative to the electrode tip 1404 and a diameter such that the filler 1416 cannot pass through coil 1450. The coil 1450 may be formed from various wires; however, in at least certain implementations, the coil 1450 is formed from a wire having a diameter from and including about 0.004 inches to and including about 0.010 inches, e.g., 0.007 inches. The coil 1450 is also preferably formed from a biocompatible material, such as MP35N steel, or otherwise coated/treated to be biocompatible.

FIG. 15 is a longitudinal sectional view of an example electrode 1500 according to the present disclosure including a third example retention element in the form of a spacer 1550 extending along the longitudinal axis 1524, which may be implemented, for example, in the feedthrough assembly 110 of the bio stimulator 100 of FIG. 1. More specifically, the electrode 1500 includes an electrode body 1502 and an electrode tip 1504 coupled to the electrode body 1502. The electrode body 1502 may further include a cup 1506 and a pin 1508 that are integrally formed such that the electrode body 1502 is monolithic. The cup 1506 can include an electrode wall 1510 extending distally from an electrode base 1512 such that the cup 1506 defines an electrode cavity 1514 within which a filler 1516 may be disposed.

To retain the filler 1516 within the electrode cavity 1514, the electrode 1500 includes a spacer 1550 disposed within the electrode cavity 1514 distal the filler 1516. In certain implementations, the spacer 1550 is a tubular spacer. In certain implementations, the spacer 1550 may be another shape, such as hexagonal. The spacer 1550 generally includes a spacer body 1552 defining a through hole 1554 through which fluid may pass to reach the filler 1516. In certain implementations, the spacer body 1550 is a tubular body. As illustrated in FIG. 15, the spacer 1550 may be disposed between the electrode tip 1504 and the filler 1516. In certain implementations, the spacer 1550 may be free floating within the electrode cavity 1514. Alternatively, the spacer 1550 may be press-fit, adhered, or otherwise fixed within the electrode cavity 1514, e.g., to an internal surface of the electrode wall 1510.

Although the dimensions and characteristics of the spacer 1550 may vary based on, among other things, the dimensions of the electrode cavity 1514 and the filler 1516, in at least certain implementations, the spacer 1550 may be a tubular spacer having a length from and including about 0.020 inches to and including about 0.040 inches, e.g., 0.030 inches, an inside diameter from and including about 0.010 inches to and including about 0.040 inches, e.g., 0.025 inches, a tube wall thickness from and including about 0.003 inches to and including about 0.010 inches, e.g., 0.008 inches, and an outside diameter from and including about 0.020 inches to and including about 0.050 inches, e.g., 0.035 inches. More generally, the spacer 1550 has a length sufficient to maintain the filler 1516 at a minimum offset relative to the electrode tip 1504, and an inside diameter such that the filler 1516 cannot pass through the through hole 1554. The spacer 1550 may be formed from various biocompatible materials; however, in at least certain implementations, the spacer 1550 is formed from MP35N steel or otherwise coated/treated to be biocompatible. In other implementations, the spacer 1550 may be formed using a resilient material such that it provides biasing similar to the spring 1350 and coil 1450 of FIGS. 13 and 14, respectively. Also, to facilitate improved fluid exchange with the filler 1516, the spacer 1550 may include grooves, channels, or similar fluid pathways (not shown) extending longitudinally along the spacer body 1552.

In certain implementations, the filler 1516 can be retained by only the spacer 1550 that allows the exposed surface area of the filler 1516 to be maximized for elution consistency.

In certain implementations, the filler 1516 can be retained by a combination of protrusions 612 in the cup 1506 of the electrode body 1502 and the spacer 1550 that allows the exposed surface area of the filler 1516 to be maximized for elution consistency. When the therapeutic agent is consistently released into the target tissue, the controlled dose can reduce inflammation associated with the device implantation.

In certain implementations, the proximal diameter of the spacer 1550 is sufficiently small to provide free space for filler 1516 to swell into, but sufficiently large to consistently hold filler 1516 in place.

Figure 16A:
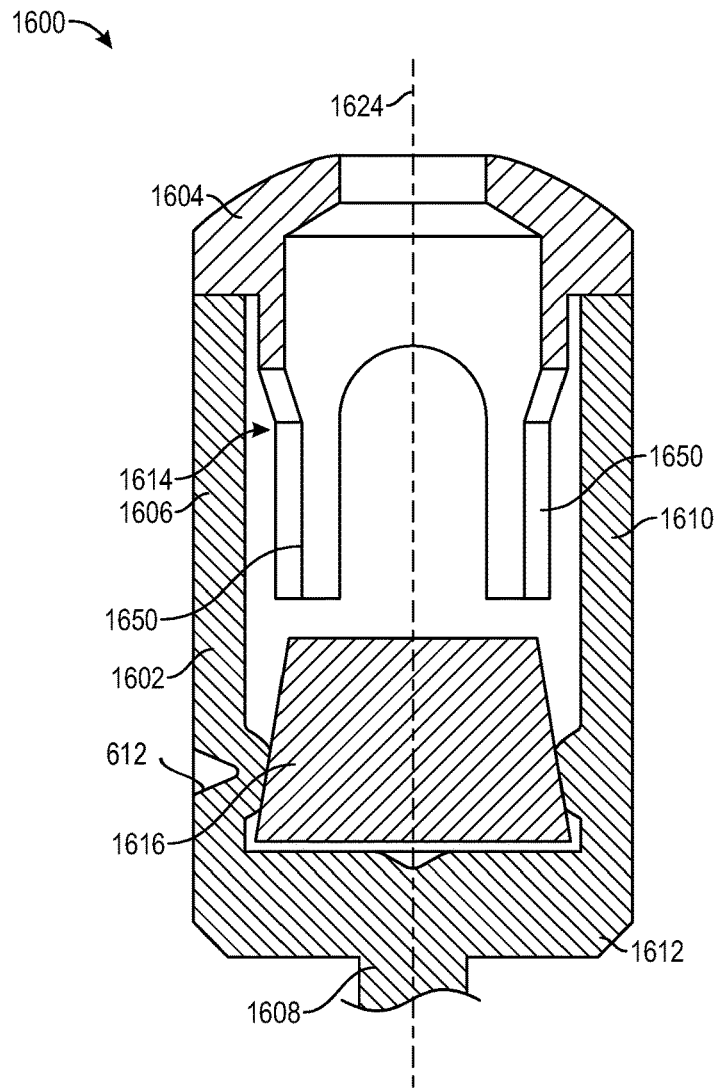
FIG. 16A is a longitudinal sectional view of still another alternative electrode according to and for use with biostimulators according to the present disclosure, the electrode including an electrode tip and a retaining element in the form of a plurality of legs extending proximally from the electrode tip.
Figure 16B:
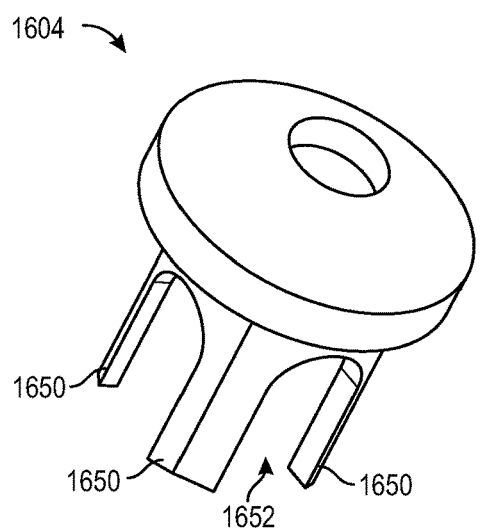
FIG. 16B is an isometric view of the electrode tip of FIG. 16A.

FIG. 16A is a longitudinal sectional view of yet another example electrode 1600 in accordance with the present disclosure that includes a fourth retention element in the form of legs 1650 extending proximally from an electrode tip 1604. More specifically, the electrode 1600 includes an electrode body 1602 and an electrode tip 1604 coupled to the electrode body 1602. The electrode body 1602 may further include a cup 1606 and a pin 1608 that are integrally formed such that the electrode body 1602 is monolithic. The cup 1606 can include an electrode wall 1610 extending distally from an electrode base 1612 such that the cup 1606 defines an electrode cavity 1614 within which a filler 1616 may be disposed. An isometric view of the electrode tip 1604 is provided in FIG. 16B.

In contrast to the previously discussed retention elements, each of which are separate components inserted into the electrode cavity 1614, the retention element of the electrode 1600 includes a plurality of legs 1650 extending proximally from the electrode tip 1604 into the electrode cavity 1614. Accordingly, when the electrode tip 1604 is coupled to the electrode body 1602 following insertion of a filler 1616 within the electrode cavity 1614, the legs 1650 extend into the electrode cavity 1614 to prevent distal movement or migration of the filler 1616.

As illustrated, the electrode tip 1604 may include four legs 1650 distributed evenly about a longitudinal axis 1624. However, in other implementations, the electrode tip 1604 may include any suitable number of legs, which may be evenly or unevenly distributed about the circumference of the electrode tip 1604. In implementations including multiple legs, gaps (e.g., gap 1652, shown in FIG. 16B) between adjacent legs 1650 may facilitate improved fluid exchange with the filler 1616.

In certain implementations, the filler 1616 can be retained by a combination of protrusions 612 in the cup 1606 of the electrode body 1602 and the legs 1650 that allows the exposed surface area of the filler 1616 to be maximized for elution consistency. When the therapeutic agent is consistently released into the target tissue, the controlled dose can reduce inflammation associated with the device implantation.

Figure 17A:
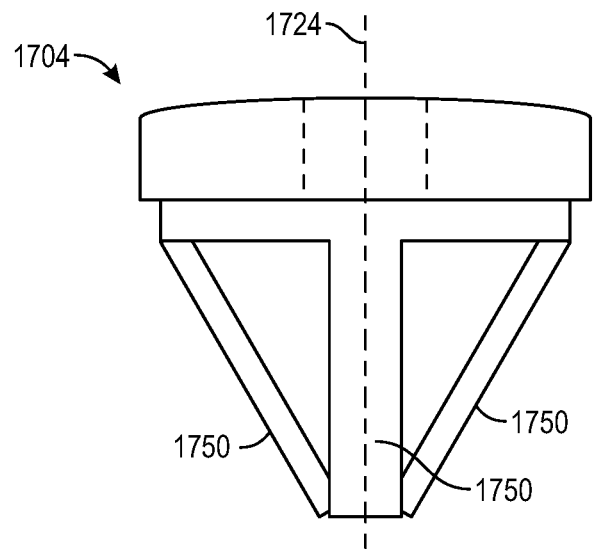
FIGS. 17A and 17B are a side elevation view and distal view, respectively of an alternative electrode tip including proximally extending legs.
Figure 17B:
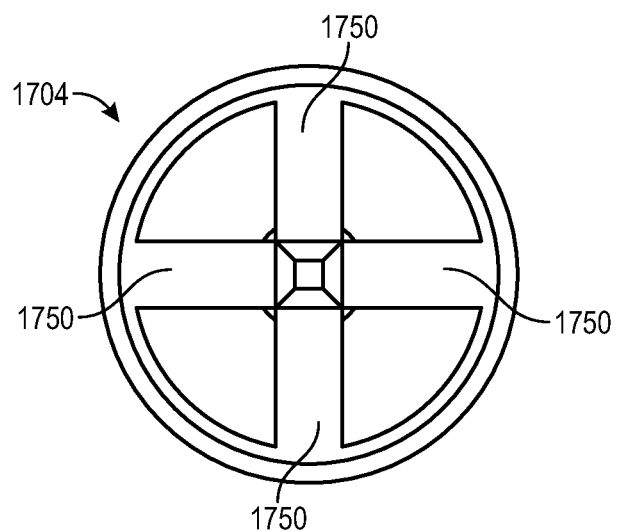

FIGS. 17A and 17B are a side view and distal view of another electrode tip 1704 which may be implemented in electrodes according to the present disclosure. Similar to the electrode tip 1604 of FIGS. 16A and 16B, the electrode tip 1704 includes a plurality of proximally extending legs 1750 such that, when assembled to an electrode body, the legs 1750 extend into an electrode cavity defined by the electrode body. In contrast to the legs 1650 of the electrode tip 1604 of FIGS. 16A and 16B, the legs 1750 extend at an angle relative to a longitudinal axis 1724 of the electrode tip 1704. By doing so, the contact area of the outer surface of the filler obstructed by the legs 1750 is minimized, thereby improving contact between the filler and fluids that enter the electrode cavity.

Figure 18:
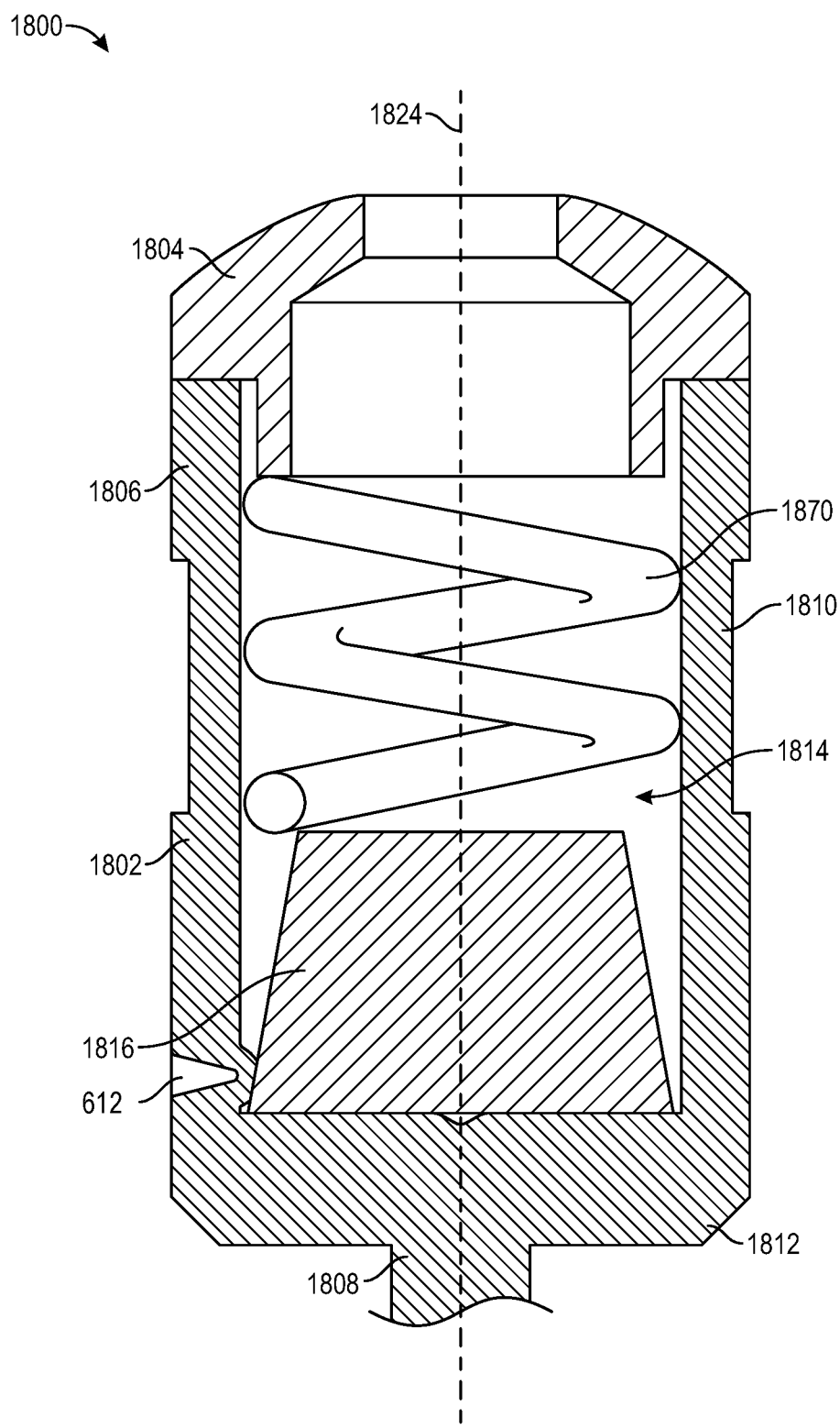
FIG. 18 is a longitudinal sectional view of another alternative electrode according to and for use with biostimulators according to the present disclosure, the electrode including multiple filler retention features in the form of internal protrusions and a coil.

Although illustrated individually in the foregoing implementations, any of the retention features discussed herein may also be used in combination. For example, FIG. 18 is a longitudinal sectional view of another example electrode 1800 according to the present disclosure that includes multiple retention features and which may be implemented, for example, in the feedthrough assembly 110 of the biostimulator 100 of FIG. 1. More specifically, the electrode 1800 includes an electrode body 1802 and an electrode tip 1804 coupled to the electrode body 1802. The electrode body 1802 further includes a cup 1806 and a pin 1808, which, in certain implementations, may be integrally formed such that the electrode body 1802 is monolithic. The cup 1806 includes an electrode wall 1810 extending distally from an electrode base 1812 such that the cup 1806 defines an electrode cavity 1814 within which a filler 1816 is disposed.

To retain the filler 1816 within the electrode cavity 1814, the electrode 1800 includes each of protrusions (e.g., protrusion 612) formed in the electrode wall 1810 and a coil 1870 disposed within the electrode cavity 1814 distal the filler 1816. In one specific implementation, the electrode 1800 may include three protrusions spaced equidistantly about a longitudinal axis 1824 of the electrode 1800 (e.g., with about 120 degrees of separation between the protrusions), each of which may generally conform to the size and dimensions of protrusions 612 described above in the context of FIG. 6. Similarly, the coil 1870 may generally conform to the coil 1450 discussed above in the context of FIG. 14.

In certain implementations, the filler 1816 can be retained by only a coil 1870 that allows the exposed surface area of the filler 1316 to be maximized for elution consistency, i.e., the cup 1806 is free of protrusions.

It should be appreciated that the example electrode 1800 combining protrusions with a coil should be regarded as non-limiting. More generally, any suitable combination of retention features may be used in implementations of the present disclosure. For example, and without limitation, any of the insertable retention elements discussed above (e.g., a spring, a coil, a tubular spacer, etc.) may be used in combination with any retention features integrally formed with the electrode wall (e.g., protrusions, tabs, an interior lip, etc.). In addition, more than one kind of insertable retention element discussed above (e.g., a spring, a coil, a tubular spacer, etc.) may be used in conjunction with each other and/or in combination with more than one kind of retention features integrally formed with the electrode wall (e.g., protrusions, tabs, an interior lip, etc.). For example, and without limitation, a spring or coil could be surrounded by a tubular spacer and used in conjunction with protrusions and/or an interior lip. In certain implementations, only one kind of retention element is used.

The foregoing description generally discusses retention features adapted to retain a filler at a predetermined location within an electrode cavity. For example, such retention features are described as being integrally formed with an electrode wall defining the cavity (e.g., in the form of one or more protrusions extending into the electrode cavity) or as elements that are inserted into the electrode cavity distal the filler. It should also be understood that the filler itself may include features configured to improve retention of the filler within the electrode cavity. For example, and without limitation, the filler may have a shape adapted to form a press fit between the electrode cavity and the filler. The filler may also include external protrusions, texturing, exterior rings/bands of a relatively high friction material, or similar exterior structures adapted to engage or provide increased friction between the filler and the electrode wall. In yet another example, the filler may be configured to expand in a controlled manner (e.g., predominantly in an outward radial direction from a longitudinal axis of the electrode cavity) as therapeutic agent is eluted from the filler so as to increase engagement between the filler and the electrode wall as the filler expands.

In implementations of the present disclosure including electrodes having multiple retention features, operations associated with manufacturing or assembling the electrode may be modified to account for the particular combination of retention features implemented. For example, and with reference to the electrode 1800 of FIG. 18, a first operation may include forming the electrode body 1802 by forming the cup 1806 and pin 1808 (which may include forming the cup 1806 and pin 1808 such that the electrode body 1802 is monolithic). Subsequent operations may include forming the protrusions 612 into the electrode wall 1810 (e.g., by indenting, swaging, or an exterior surface of the electrode wall 1810) and inserting the filler 1816 into the electrode cavity 1814 such that the filler 1816 is in contact with the protrusions 612. The coil 1870 may then be inserted into the electrode cavity 1814 distal the filler 1816 such that the coil 1870 contacts the filler 1816. The electrode 1800 may then be capped by inserting the electrode tip 1804 and joining the electrode tip 1804 with the electrode body 1802, thereby sealing the electrode cavity 1814 with the filler 1816 and coil 1870 contained therein.

The foregoing operations are intended as a non-limiting example based on an example electrode including retention features in the form protrusions and a coil. It should be appreciated that the operations may be modified (e.g., by changing the order of the operations) to accommodate any combination of the retention features discussed herein.

In the foregoing specification, aspects of the present disclosure have been described with reference to specific exemplary implementations thereof. It will be evident that various modifications may be made thereto without departing from the broader spirit and scope of the disclosure. The specification and drawings are, accordingly, to be regarded in an illustrative sense rather than a restrictive sense.

Reference signs are not to be construed as limiting the extent of the matter protected by the claims; their sole function is to make claims easier to understand.

What is claimed is:

1. An electrical feedthrough assembly for a biostimulator, comprising:
an electrode body including a cup having an electrode wall extending distally from an electrode base around an electrode cavity located on a longitudinal axis, and a pin extending proximally from the electrode base along the longitudinal axis, wherein the cup and the pin are integrally formed from a single blank of material such that the electrode body is monolithic.

2. The electrical feedthrough assembly of claim 1 further comprising:
an insulator having an insulator wall extending distally from an insulator base around the electrode wall, wherein the insulator base is proximal to the electrode base, wherein an insulator hole extends through the insulator base along the longitudinal axis, wherein the pin has a distal pin end at a proximal face of the electrode base, and wherein the pin extends through the insulator hole from the proximal face of the electrode base to a proximal end of the electrode body; and
a flange having a mounting wall extending around the insulator wall.

3. The electrical feedthrough assembly of claim 2 further comprising a gasket having an annular body extending around the electrode wall, wherein the gasket is distal to the insulator wall and the mounting wall, and wherein the gasket includes a resilient material.

4. The electrical feedthrough assembly of claim 1 further comprising an electrode tip mounted on a distal end of the electrode body, wherein the electrode tip includes a tip hole extending through the electrode tip along the longitudinal axis from a distal tip end to a proximal tip end, and wherein a first diameter of the tip hole at the distal tip end is less than a second diameter of the tip hole at the proximal tip end.

5. The electrical feedthrough assembly of claim 4 further comprising one or more weeping holes extending through one or more of the electrode wall or the electrode tip along a transverse axis orthogonal to the longitudinal axis.

6. The electrical feedthrough assembly of claim 1 further comprising a filler in the electrode cavity, wherein the filler includes a therapeutic agent in a silicone matrix.

7. The electrical feedthrough assembly of claim 6, wherein the electrode wall includes one or more protrusions in contact with an outer surface of the filler.

8. The electrical feedthrough assembly of claim 7, wherein the one or more protrusions include a plurality of protrusions spaced equidistantly about the longitudinal axis.

9. The electrical feedthrough assembly of claim 6, further comprising a coil disposed within the electrode cavity distal the filler, wherein the coil extends along the longitudinal axis and is in contact with the outer surface of the filler.

10. A biostimulator, comprising:
a housing having a longitudinal axis and containing an electronics compartment;
an electronics assembly mounted in the electronics compartment, wherein the electronics assembly includes an electrical connector; and
an electrical feedthrough assembly mounted on the housing, wherein the electrical feedthrough assembly includes an electrode body including a cup having an electrode wall extending distally from an electrode base around an electrode cavity located on the longitudinal axis, and a pin extending proximally from the electrode base along the longitudinal axis into contact with the electrical connector of the electronics assembly, and wherein the cup and the pin are integrally formed from a single blank of material such that the electrode body is monolithic.

11. The biostimulator of claim 10, wherein the electrical feedthrough assembly further includes:
an insulator having an insulator wall extending distally from an insulator base around the electrode wall, wherein the insulator base is proximal to the electrode base, wherein an insulator hole extends through the insulator base along the longitudinal axis, wherein the pin has a distal pin end at a proximal face of the electrode base, and wherein the pin extends through the insulator hole from the proximal face of the electrode base to the electrical connector; and
a flange mounted on the housing and having a mounting wall extending around the insulator wall.

12. The biostimulator of claim 11 further comprising:
a helix mount mounted on the flange; and
a gasket having an annular body extending around the electrode wall, wherein the annular body is resiliently compressed between the helix mount and the mounting wall.

13. The biostimulator of claim 12 further comprising:
a fixation element mounted on the helix mount, wherein the fixation element includes a helix revolving about the longitudinal axis in a first rotational direction;
wherein the helix mount is mounted on the flange by a threaded connection having threads revolving about the longitudinal axis in a second rotational direction opposite to the first rotational direction.

14. The biostimulator of claim 10 further comprising an electrode tip mounted on a distal end of the electrode body, wherein the electrode tip includes a tip hole extending through the electrode tip along the longitudinal axis from a distal tip end to a proximal tip end, and wherein a first diameter of the tip hole at the distal tip end is less than a second diameter of the tip hole at the proximal tip end.

15. The biostimulator of claim 10 further comprising a filler in the electrode cavity, wherein the filler includes a therapeutic agent in a silicone matrix.

16. The biostimulator of claim 15, wherein the electrode wall includes one or more protrusions in contact with an outer surface of the filler.

17. The biostimulator of claim 16, wherein the one or more protrusions include a plurality of protrusions spaced equidistantly about the longitudinal axis.

18. The biostimulator of claim 17 further comprising a coil disposed within the electrode cavity distal the filler, wherein the coil extends along the longitudinal axis and is in contact with the outer surface of the filler.

19. A method, comprising:
forming, from a blank of material, a distal portion of an electrode body, wherein the distal portion includes a cup having an electrode wall extending distally from an electrode base around an electrode cavity located on a longitudinal axis; and
forming, from the blank of material, a proximal portion of the electrode body, wherein the proximal portion includes a pin that is integral to the cup, and wherein the pin extends proximally from the electrode base along the longitudinal axis.

20. The method of claim 19 further comprising:
inserting the pin through an insulator hole of an insulator; and
bonding the pin to the insulator by a braze joint.

21. The method of claim 20 further comprising:
inserting the insulator into a mounting hole in a flange; and
bonding the insulator to the flange by a second braze joint.

22. The method of claim 21 further comprising:
forming one or more protrusions on an inner surface of the electrode wall; and
inserting a filler in the electrode cavity to place the one or more protrusions in contact with an outer surface of the filler.

23. The method of claim 21 further comprising inserting a coil in the electrode cavity distal the filler such that the coil is in contact with the outer surface of the filler.

24. The method of claim 23 further comprising:
mounting an electrode tip on a distal end of the electrode body, wherein the electrode tip includes a tip hole extending through the electrode tip along the longitudinal axis from a distal tip end to a proximal tip end within the electrode cavity, and wherein a first diameter of the tip hole at the distal tip end is less than a second diameter of the tip hole at the proximal tip end.

\* \* \* \* \*